(12) United States Patent
Xiao et al.

(10) Patent No.: US 9,096,430 B2
(45) Date of Patent: Aug. 4, 2015

(54) METHOD FOR METAL NANOPARTICLE ELECTROCATALYTIC AMPLIFICATION

(75) Inventors: Xiaoyin Xiao, Austin, TX (US); Allen J. Bard, Austin, TX (US); Fu-Ren F. Fan, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1154 days.

(21) Appl. No.: 12/139,280

(22) Filed: Jun. 13, 2008

(65) Prior Publication Data

US 2009/0065371 A1    Mar. 12, 2009

Related U.S. Application Data

(60) Provisional application No. 60/943,771, filed on Jun. 13, 2007.

(51) Int. Cl.
*G01F 1/64* (2006.01)
*B82Y 5/00* (2011.01)
*B82Y 15/00* (2011.01)
*B82Y 30/00* (2011.01)
*G01N 27/327* (2006.01)

(52) U.S. Cl.
CPC . *B82Y 5/00* (2013.01); *B82Y 15/00* (2013.01); *B82Y 30/00* (2013.01); *G01N 27/3278* (2013.01)

(58) Field of Classification Search
CPC .......... B82Y 5/00; B82Y 15/00; B82Y 30/00; G01N 27/3278
USPC ............. 204/403.01–403.15; 205/787, 777.5, 205/778, 790.5, 775; 436/6; 977/880
See application file for complete search history.

(56) References Cited

U.S. PATENT DOCUMENTS

| | | | |
|---|---|---|---|
| 5,571,401 A * | 11/1996 | Lewis et al. | 205/787 |
| 6,537,498 B1 | 3/2003 | Lewis et al. | |
| 6,686,150 B1 | 2/2004 | Blackburn et al. | |
| 6,972,173 B2 | 12/2005 | Su et al. | |
| 2004/0157263 A1 | 8/2004 | Diessel et al. | |

(Continued)

FOREIGN PATENT DOCUMENTS

| | | |
|---|---|---|
| JP | 2004-1329854 | 4/2004 |
| WO | 01/00876 | 1/2001 |
| WO | 2008/157403 | 12/2008 |

OTHER PUBLICATIONS

International Search Report and Written Opinion for PCT/US08/66983 dated Jun. 13, 2008.

(Continued)

*Primary Examiner* — Keith Hendricks
*Assistant Examiner* — Kourtney S Carlson
(74) *Attorney, Agent, or Firm* — Chainey P. Singleton; Edwin S. Flores; Chalker Flores, LLP

(57) ABSTRACT

The present invention includes methods, compositions and kits for analyzing a chemical analyte having an electrochemical cell connected to a measuring apparatus. The electrochemical cell contains a solution having one or more nanoparticles, one or more chemical analytes, an indicator. In addition, the electrochemical cell contains one or more electrodes in communication with the solution. One or more electrocatalytic properties are generated by the interaction of the one or more nanoparticles and the liquid sample and measured at the one or more electrodes.

16 Claims, 24 Drawing Sheets

(56) References Cited

U.S. PATENT DOCUMENTS

2005/0084881 A1*  4/2005  Kelley et al. .................. 435/6
2007/0034529 A1*  2/2007  Bard et al. .................. 205/775

OTHER PUBLICATIONS

Gill, R., et al., "Pt Nanoparticles Functionalized with Nucleic Acid Act as Catalytic Labels for the Chemiluminescent Detection of DNA and Proteins," Small (2006), 2:1037-1041.

Niazov, T., et al. "Photoswitchable Electrocatalysis and Catalyzed Chemiluminescence Using Photoisomerizable Monolayer-Functionalized Surfaces and Pt Nanoparticles," J Am Chem Soc (2007), 129:6374-6375.

Polsky, R., et al., "Nucleic Acid-Functionalized Pt Nanoparticles: Catalytic Labels for the Amplified Electrochemical Detection of Biomolecules," Anal. Chem. (2006), 78:2268-2271.

Sonnichsen, C., et al., "A Molecular Ruler Based on Plasmon Coupling of Single Gold and Silver Nanoparticles," Nature Biotechnology (2005), 23:741-745.

Xiao, X., et al., "Measurement of Single Molecule Conductance: Benzenedithiol and Benzenedinnethanethiol," Nano Letters (2004), 4:267-271.

Yang, J., "Size effect in thiol and amine binding to small Pt nanoparticles," Analytica Chimica Acta (2006), 571:206-210.

Zhou, J., et al., "Scanning electrochemical microscopy Part 39. The proton:hydrogen mediator system and its application to the study of the electrocatalysis of hydrogen oxidation," J Electroanal Chem (2000), 491:22-29.

International Preliminary Report on Patentability for PCT/US2008/066983 dated Sep. 3, 2008, 6 pp.

Machine translation of Japan Publication No. 2005-227154, dated Aug. 25, 2005, 24 pp.

Krapf, et al. "Fabrication and Characterization of Nanopore-Based Electrodes with Radii down to 2 nm" Nano Lett. 2006, 6, 105-109.

Tel-Vered, et al. "Generation and Detection of Single Metal Nanoparticles Using Scanning Electrochemical Microscopy Techniques" J. Phys. Chem. B 2006, 110, 25279-25287.

Chen, et al. "Gold Nanoelectrodes of Varied Size: Transition to Molecule-Like Charging" Science, Jun. 26, 1998, 280, 2098-2101.

Narayanan, et al. "Catalysis with transition metal nanoparticles in colloidal solution: nanoparticle shape dependence and stability" J. Phys. Chem. B 2005, 109, 12663-12676.

Harnisch, et al. "Attachment of Gold Nanoparticles to Glassy Carbon Electrodes via a Mercaptobenzene Film" J. Am. Chem. Soc., May 25, 2001, 123, 5829-5830.

Fan, et al. "An Electrochemical Coulomb Staircase: Detection of Single Electron-Transfer Events at Nanometer Electrodes" J. Science, Sep. 19, 1997, vol. 277, 1791-1793.

Chen, et al. "Electrodeposition of Platinum on Nanometer-Sized Carbon Electrodes" J. Phys. Chem. B, Jul. 23, 2003, 107, 8392-8402.

Bobbert, et al. "Diffusion to a slowly growing truncated sphere on a substrate" J. Physica 1987, 141A, 58-72.

* cited by examiner

This application claims priority to U.S. Provisional Application Ser. No. 60/943,771, filed Jun. 13, 2007, the content of which is incorporated by reference herein in its entirety.

STATEMENT OF FEDERALLY FUNDED RESEARCH

This invention was made with U.S. Government support under Contract No. CHE 0451494 awarded by the National Science Foundation. The government has certain rights in this invention.

TECHNICAL FIELD OF THE INVENTION

The present invention relates in general to the field of nanoparticles; and in particular, the present invention relates to instruments, methods and reagents for amplifying a signal from a catalytic reaction using metal nanoparticles.

BACKGROUND OF THE INVENTION

Without limiting the scope of the invention, its background is described in connection with nanoparticles. The physical properties (e.g., high surface-to-volume ratio, elevated surface energy, increased ductility after pressure loading, higher hardness, larger specific heat and the like) of nanoparticles have let to increased applications in the material-directed industry and material science. For example, a variety of metal nanoparticles have been used to catalyze numerous reactions.

The size of nanoparticles range from the 0.5 to 100 nm and the electronic energy band configuration is a size-dependent property, which in turn affect the physical and chemical properties. A fundamental distinction between nanoparticles and their bulk materials is that the fraction of surface atoms and the radius of curvature of the surface are comparable with the lattice constant. As a result, the nanostructured catalysts have a higher catalytic activity of as compared with their analogues based on bulk materials. The methods of forming nanoparticles are known to the skilled artisan and include formation by combining atoms (or more complex radicals and molecules) and by dispersion of bulk materials, e.g., thermal evaporation, ion sputtering, reduction from solution, reduction in microemulsions and condensation.

For example, U.S. Pat. No. 6,537,498 entitled, "Colloidal particles used in sensing arrays" discloses chemical sensors for detecting analytes in fluids having a plurality of alternating nonconductive regions and conductive regions of conductive nanoparticle materials. Variability in chemical sensitivity from sensor to sensor is provided by qualitatively or quantitatively varying the composition of the conductive and/or nonconductive regions.

Another example includes U.S. Pat. No. 6,972,173 entitled, "Methods to increase nucleotide signals by Raman scattering" teaches methods and apparatus relating to nucleic acid sequencing by enhanced Raman spectroscopy using nucleotides covalently linked to silver or gold nanoparticles. Electrocatalysis at nanoparticles, for analytical purposes, has been described in the art; however, such descriptions involve large numbers of nanoparticles, at least hundreds of thousands, as monolayer or near monolayer films on electrode surfaces.[1]

SUMMARY OF THE INVENTION

The present inventors recognized the difficulties in generating, locating and characterizing a single nanoparticle electrochemically, especially at the nm scale and in measuring the very small currents or charges associated with these electrode reactions.

The present invention provides a method and apparatus for observing electrochemically the collisions of single nanoparticles (NPs) at an electrode. The present invention provides electrocatalysis at single nanoparticles, as well as the basis of highly sensitive electroanalytical methods. Metal, carbon, and semiconductor nanoparticles have a wide range of applications in electronics, optics and catalysis.

The present invention relates to a method and device of analyzing a sample within a sample chamber. The method of the present invention include adding one or more nanoparticles to a liquid sample within a sample chamber, and observing one or more electrocatalytic properties generated by the interaction of the nanoparticles and the liquid sample using one or more electrode. Typically, the electrocatalytic property is an amplification of a reaction catalyzed by the metal nanoparticles; however, the electrocatalytic property may also include, but not limited to a current, a resistance, an impedance, a capacitance, an inductance or any combinations thereof, or any other means of recognizing an electron transfer event at an electrode.

In addition, the present invention includes the use of nanoparticles to detect and analyze biological molecule. For example, a molecule (e.g., an antibody, polynucleotide, single-strand DNA or RNA) of interest may be linked or labeled with nanoparticles that interact with or adhere to the electrode surface to bring the nanoparticles in close proximity to the electrode where its electrocatalytic properties are used in detection and analysis.

The device of the present invention includes an electrochemical cell connected to a measuring apparatus. The electrochemical cell typically has one or more electrodes, one or more nanoparticle deposited in a sample chamber, and a detector in communication with the electrodes. The deposited nanoparticles interact with the sample and generate one or more electrocatalytic properties that can be picked up by the detector. The device may optionally contain an indicator in a solution. In addition, the electrochemical cell may have a dimension in the nanometer scale with ultramicroelectrodes.

The present invention includes a kit for analyzing one or more chemical analyte(s) having at least one nanoparticle, at least one chemical indicator, at least one electrode, and a measuring apparatus that reads one or more electrocatalytic property generated by the interactions between the nanoparticle(s), the electrode(s) and the chemical analyte(s).

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
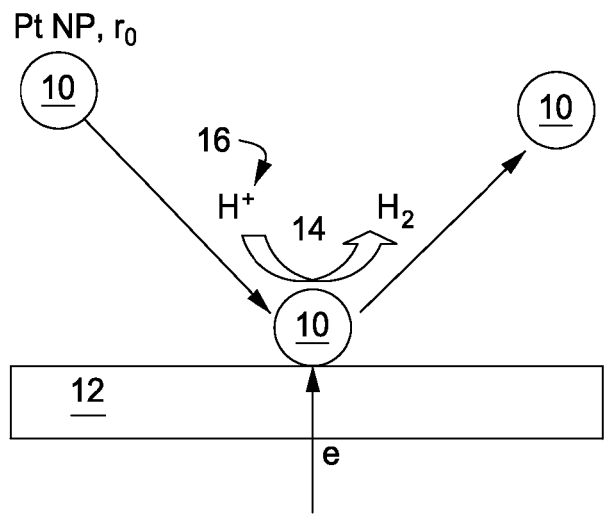
FIG. 1 is a schematic of the platinum nanoparticle collision event.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "linked" or "linking" refers to an association between two moieties. The association can be a covalent bond. The association can be a non-covalent bond, including but not limited to, ionic interactions, hydrogen bonds, and van der Waals forces. Exemplary non-covalent bonds include hybridization between complementary oligonucleotides and/or polynucleotides, biotin/streptavidin interactions, and antibody/antigen interactions.

As used herein, the term "nanoparticle" as used herein refers to an individual nanoparticle, unless otherwise indicated. Nanoparticles, as disclosed herein, are materials with dimensions at the nanoscale, which ranges from about 0.5 nm to about 100 nm. According to the present disclosure, nanoparticles may comprise metals as well as nonmetals, and may be coated or capped. The term "nanoparticle" according to the invention does not encompass biological compounds.

As used herein, the term "electrode" as used herein refers to an electrically conductive measuring part of an electrochemical cell. As disclosed herein, the electrode is a poor electrocatalyst for the redox reactant and is sufficiently conductive to enable charge transfer to contacting nanoparticles.

As used herein, the term "contact" as used herein refers to two objects being within the tunneling distance of one another. Within this distance, charge transfer can occur.

As used herein, the term "redox reactant" as used herein, refers to a material in an electrochemical cell, distinct from the nanoparticle and the electrode that is capable of undergoing a reduction or oxidation reaction.

As used herein, the term "linked" or "linking" refers to an association between two moieties. The association can be a covalent bond. The association can be a non-covalent bond, including but not limited to, ionic interactions, hydrogen bonds, and van der Waals forces. Exemplary non-covalent bonds include hybridization between complementary oligonucleotides and/or polynucleotides, biotin/streptavidin interactions, and antibody/antigen interactions.

As used herein, the term "electrocatalyst" as used herein refers to a material that is capable of amplifying the rate of electrochemical oxidation or reduction of a redox reactant. In at least one embodiment, contact between a nanoparticle and an electrode enables charge transfer between the nanoparticle and the electrode and enables the nanoparticle to become an electrocatalyst for the redox reactant.

As used herein, the term "trace amount" as used herein means that a material is present, if at all, in an amount that cannot measurably contribute to an electrocatalytic reaction.

The present invention provides methods based on the large current amplification factor involved in a rapid electrocatalytic reaction of a species in single particle collision events. The reaction of the species at a relatively high concentration in solution at the nanoparticle does not occur at the conductive, but not catalytic, measuring ultramicroelectrode (UME). The skilled artisan will recognize that the measuring microelectrode surface can be treated to decrease the activity for a particular electrode reaction, for example by forming an oxide film or adsorbing certain compounds. The electrode can also be treated to promote the adsorption or sticking of the catalytic particle and this can provide the basis of various analytical schemes.

FIG. 1 is a schematic of a single platinum nanoparticle collision event. The particle diffuses to the electrode where it collides and catalyzes a reduction (in this schematic of a proton) during the residence time. The collisions of single platinum nanoparticles 10 at an ultramicroelectrode 12 were observed electrochemically by their characteristic current-time transients for a particle-catalyzed reaction 14. A single event is characterized by the current generated by an electrocatalyzed reaction of an indicator species 16 (e.g., proton, hydrogen peroxide) present in solution. Since the indicator reaction 14 does not occur at the selected ultramicroelectrode 12 and can involve a high concentration of indicator species 16 with a much larger diffusion coefficient than the nanoparticle 10, large amplification (e.g., ten orders of magnitude or more) in the current occurs. Every collision produces a unique current-time profile that can be correlated with the particle size, the particle residence time and the nature of the nanoparticle 10 interaction with the ultramicroelectrode 12 surface. The present invention also allows the study of heterogeneous kinetics at single nanoparticles 10, determination of particle size distributions and the application of very sensitive electroanalytical technique. While this example describes herein is reduction reaction, one schooled in the art will recognize that the same principle holds for a catalyzed oxidation reaction, for example of methanol, at the appropriate potential of UME with a platinum particle.

Figure 2:
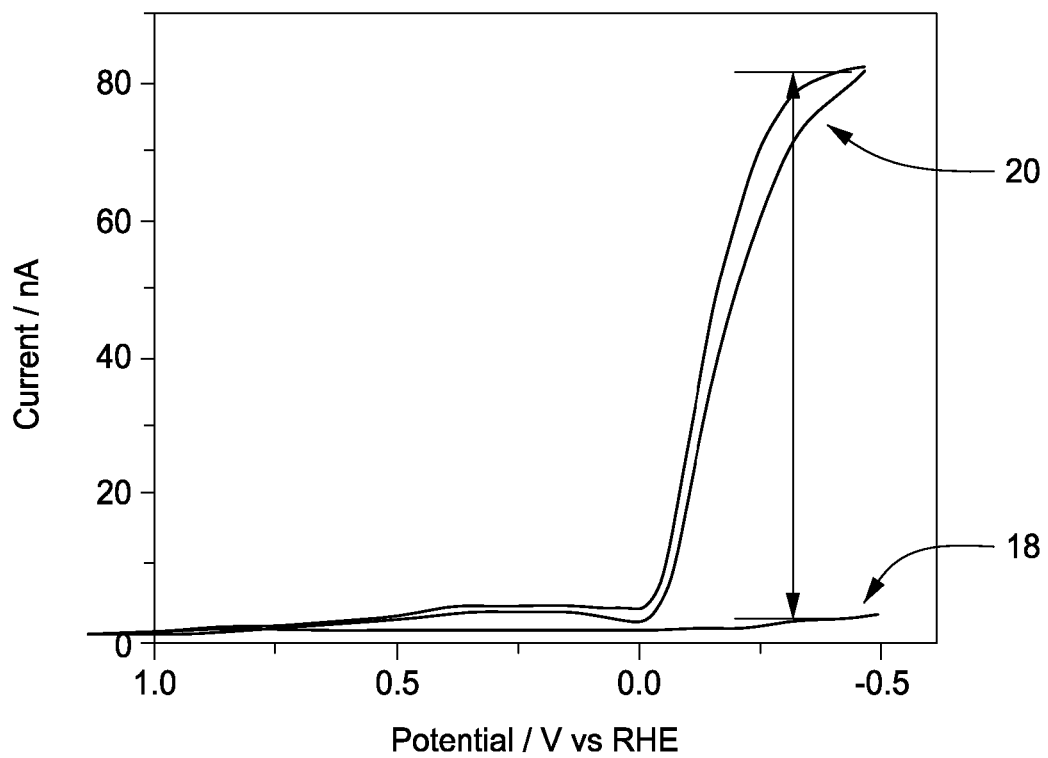
FIG. 2 is a graph of the electrochemical reduction of proton at carbon fiber electrode with and without Pt nanoparticles.

FIG. 2 is a graph of the electrochemical reduction of proton at a disk carbon fiber in glass electrode without in the lower curve 18 and with platinum nanoparticles in the upper curves 20 on the surface in air-saturated, 50 mM sodium dihydrogencitrate solution, fiber diameter: 8 μm, sweep rate: 100 mV/s). The electrode is made by sealing an 8 μm diameter carbon fiber in soft glass and then polishing the bottom so that only a disk of carbon is exposed to the solution. As an example, consider a carbon fiber ultramicroelectrode immersed in a dispersion of platinum nanoparticles in an acidic aqueous solution. The steady-state diffusion-controlled flux of particles to the ultramicroelectrode surface, $J_{p,s}$, is given by:

$$J_{p,s} = 4D_p C_p / \pi a \quad (1)$$

where $D_p$ is the particle diffusion coefficient, $C_p$ the particle concentration, and a is the radius of the carbon ultramicroelectrode disk electrode.[2] Ordinarily, in the simple nanoparticles charging process, only one or a few electrons would transfer between the nanoparticles and the ultramicroelectrode ($n_p$) to yield a current, $i_{p,s} = n_p F \pi a^2 J_{p,s}$, that is much too small to observe above the noise and background level (where F is the Faraday). However, the nanoparticles can electrocatalyze another reaction of an indicator species (e.g., proton, hydrogen peroxide), and a reduction of a species O to R, upon contact with the ultramicroelectrode (e.g. hydrogen evolution at a platinum particle), a much larger current, $i_O$, can flow. That is, when the nanoparticles collide with the electrode surface, it allows the reaction of O to R at a potential where this reaction does not occur at the ultramicroelectrode. For example, if the particle sticks to the ultramicroelectrode surface after a collision, the steady-state diffusion-controlled current at a particle is given by:

$$i_{O,p} = n_O F A_p J_{O,p} = B n_O F D_O C_O r_0 \quad (2)$$

where $J_{O,p}$ is the flux of O to the particle, $D_O$ is the diffusion coefficient of O in the solution, $C_O$ the concentration of O, and $r_0$ the radius of the particle. The factors, $A_p$, the particle area, and B, depend on the particle shape and how it is situated on the ultramicroelectrode. If it can be considered a sphere on an infinite plane, then $A_p = 4\pi r_0^2$ and $B = 4\pi \ln 2 = 8.71$. Since $C_O$ and $D_O$ can be much larger than $C_p$ and $D_p$, even with the difference in a and $r_0$, the diffusional flux of O to a single particle can be ten orders of magnitude or more larger than that of particles to the ultramicroelectrode.

The current for a collision is a transient that includes particle charging and a changing faradaic current for O reduction that attains steady state in a time $\sim r_0^2 / D_O$. Since different types of collisions can occur, the current-time (i-t) transient for each collision event will be determined by the residence time, τ, of the particle at the electrode, i.e., the time period when the electrode can pass electrons to the particle. If the particle sticks to the electrode for a time sufficient for a steady state current to be attained, and the reactant O is only reduced at the particle, an amplification factor given by the relative steady-state fluxes of the particles and O, is $\sim (B/16)(D_O C_O a)/(D_p C_p r_0)$. This will lead to relative steady-state currents of $\sim B(D_O C_O r_0)/4(D_p C_p a)$ (assuming $n_p = n_O$). For a 1 pM particle solution and 10 mM indicator O, the estimated amplification factor for a 1 nm radius particle can be nine to ten orders of magnitude, assuming the diffusion coefficient of reactant O and that of the particle are different by about an order of magnitude.

Two electrochemical reactions, the reduction of proton and the reduction of hydrogen peroxide, were chosen to illustrate this effect. The skilled artisan will recognize that other materials may be used that undergo catalyzed reduction or oxidation. Both of these reactions are sluggish at a carbon ultramicroelectrode but are more rapid at the platinum. As shown in FIG. 2, proton reduction does not occur at a carbon electrode in 50 mM sodium dihydrogen citrate (NaH$_2$Citr) at potentials positive of −0.5 V vs SHE, the small increase in current between 0 and −0.5 V is due to some reduction of oxygen in the solution. For a carbon electrode covered with Pt particles or a pure platinum electrode, proton reduction gives rise to a steady-state current at potentials more negative than −0.3 V.[3] At these potentials, oxygen reduction is also significantly promoted. The steady-state current at a platinum particle can be estimated from the steady-state current to a sphere in contact with a nonreacting plane, provided the particle maintains ohmic contact with the ultramicroelectrode and the applied potential is sufficient to change O to R under diffusion control. This current for proton reduction under the described conditions should be about 30 pA for a spherical particle of 2 nm in diameter. Higher currents per particle could be achieved by increasing the proton concentration, for example, using higher concentrations of sodium dihydrogencitrate or tens millimolar concentration of perchloric acid (must be less than 60 mM to prevent formation of hydrogen bubbles), however the particles would aggregate and precipitate under these conditions as seen in FIG. 3.

Figure 3A:
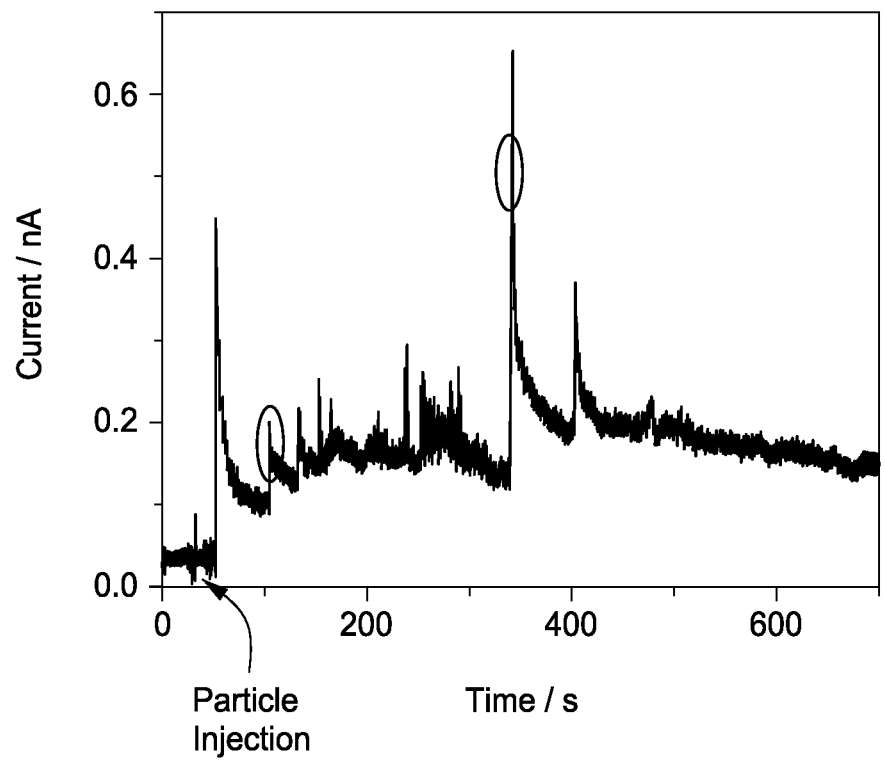
FIG. 3A is a graph of the current transition before and after injection of platinum colloidal solution at the carbon fiber electrode.
Figure 3B:
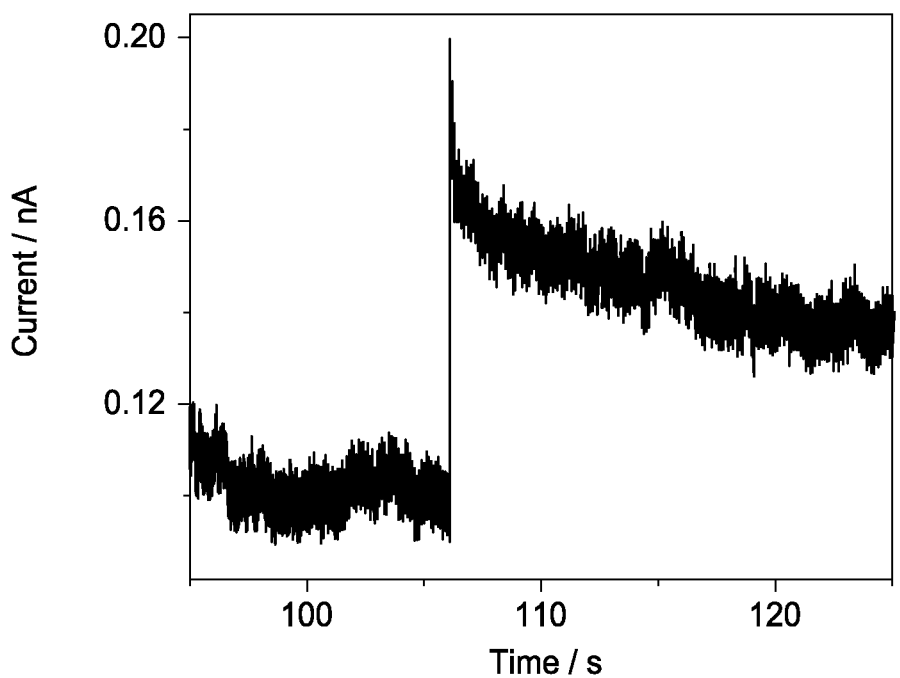
FIG. 3B is a graph that indicates the sticking of a single particle.
Figure 3C:
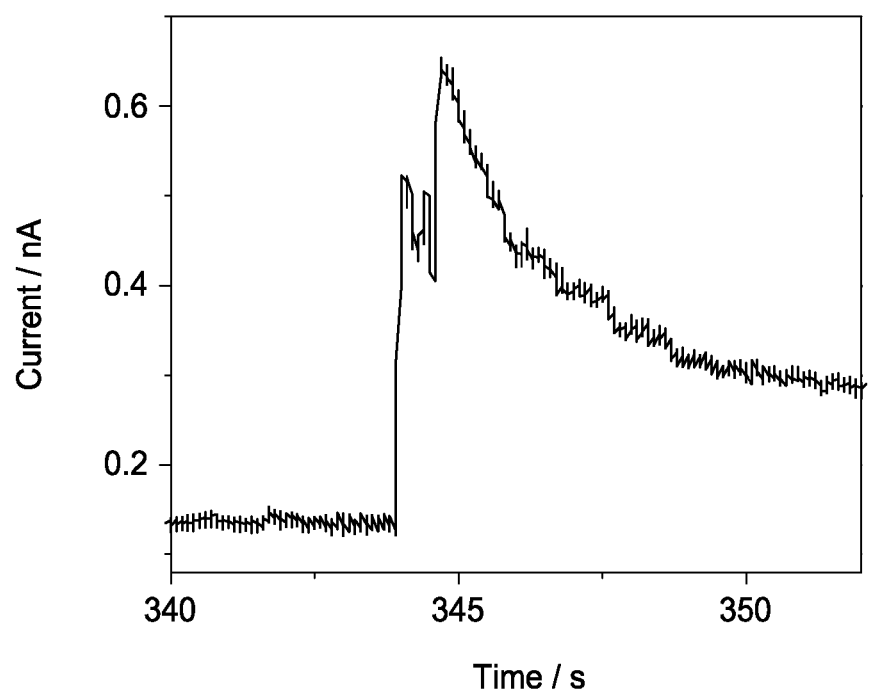
FIG. 3C is a graph that shows the sticking of a particle aggregate.

FIG. 3A is a graph of the current transition before and after injection of platinum colloidal particle solution at the carbon fiber electrode in 20 mM HClO$_4$ and 0.1 M NaClO$_4$. The FIG. 3B is a graph that indicates the sticking of a single particle and FIG. 3C is a graph that shows a particle aggregate.

Figure 4A:
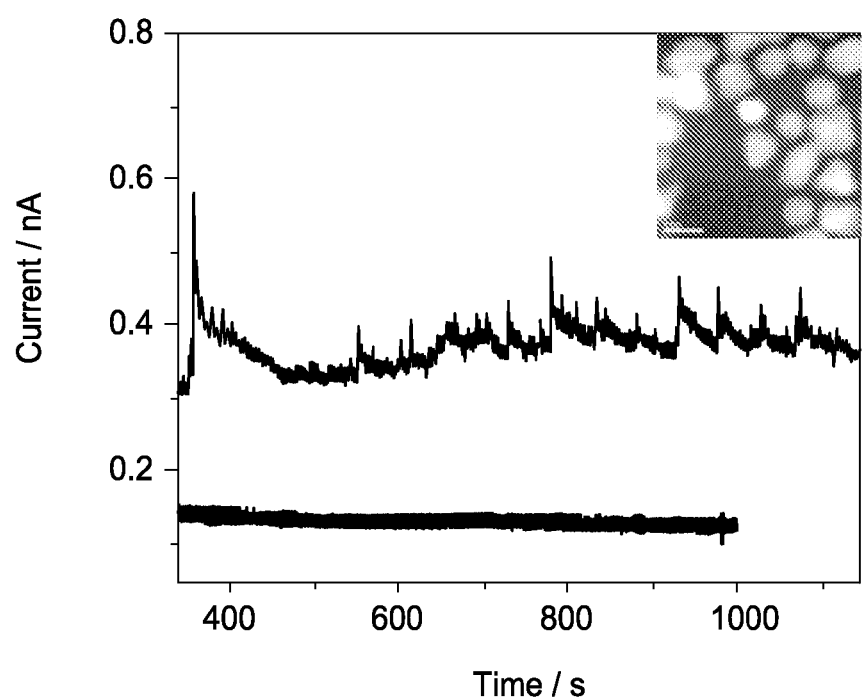
FIGS. 4A and 4B are graphs of current transients at a carbon electrode in a solution before and after injecting platinum particles.
Figure 4B:
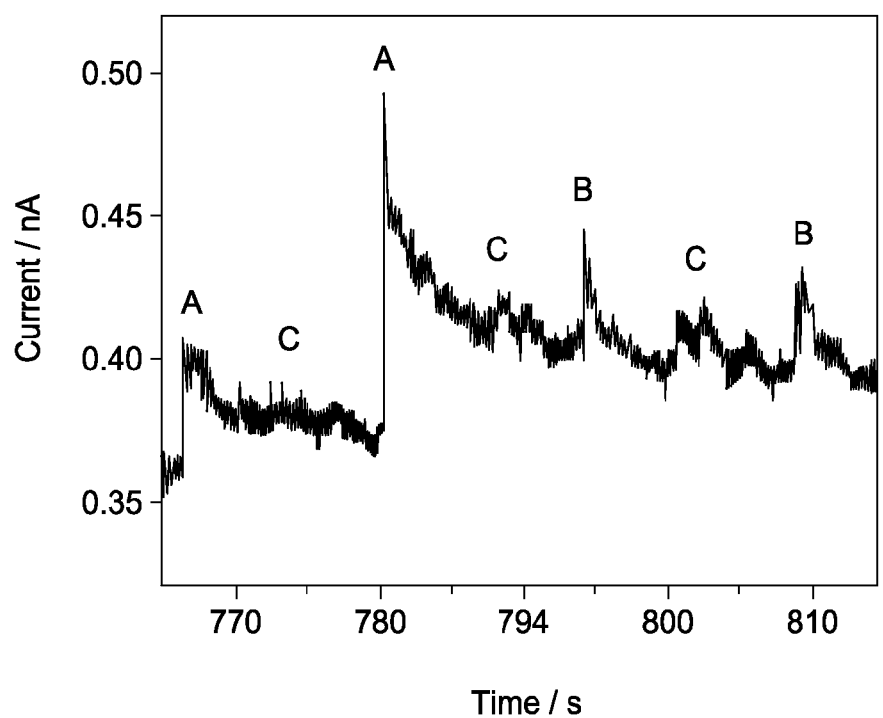
Figure 4C:
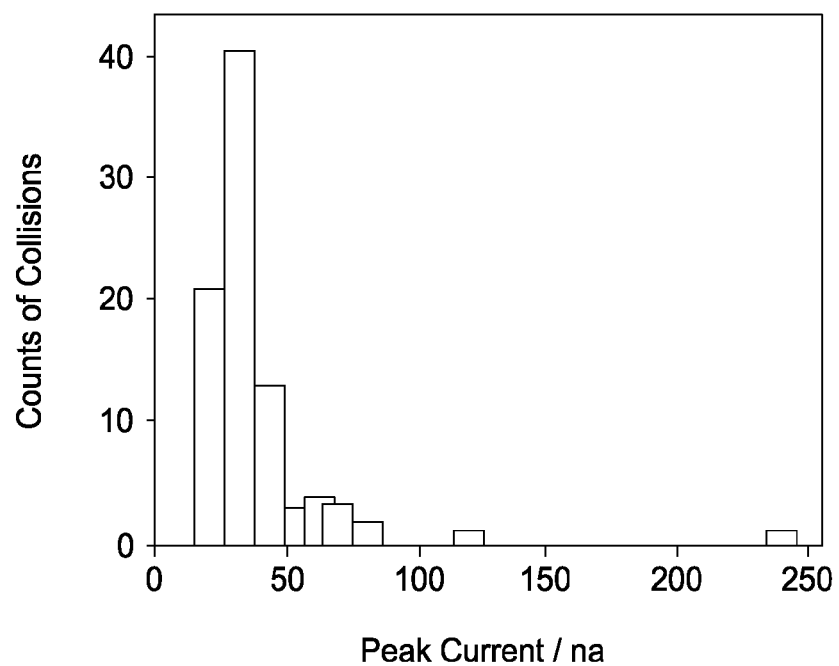
FIG. 4C is a plot of the statistics of number of collisions versus their peak currents.

FIG. 4 shows the current transients at a carbon electrode in a solution before and after injecting platinum particles. FIG. 4A is a graph of the current transients at a carbon fiber electrode in 50 mM sodium dihydrogencitrate solution in the absence of platinum citrate nanoparticles seen in the bottom curve 22 and presence of platinum citrate nanoparticles seen in the top curve 24. Particle concentration is about 50 pM. FIG. 4B is a graph of a magnified portion of FIG. 4A showing three kinds of collisions distinguished by the current, amplitude and frequency: A, B and C respectively. FIG. 4C is a plot of the statistics of number of collisions versus their peak currents. Collisions with peak currents less than 15 pA, which were typically frequency (C) type, are not included and collisions with peak current larger than 40 pA are mostly due to sticking of the particles. Inset is a TEM image of representative platinum nanoparticles.

The carbon ultramicroelectrode potential was −0.4 V. The platinum colloidal solution was obtained by reducing $H_2PtCl_6$ with sodium borohydride in the presence of sodium citrate.[4] The particle sizes had a range of between about 2 to 6 nm, with a major distribution at 4±0.8 nm in diameter. Typically about 2, 5, and 10 µL colloidal solutions (initially 0.5 mM in $H_2PtCl_6$ before reduction to form the nanoparticles) were injected sequentially into a about 50 mL electrochemical cell under nitrogen bubbling, resulting in pM solutions of nanoparticles and then the i-t responses were recorded under a nitrogen atmosphere. Before injection of the particle solution, the current transient was a smooth curve with a small constant noise level, while after injection, large current transients appeared. These fluctuations are due to the collisions of particles with the supporting electrode. The amplitude of the steady-state current for the irreversible collisions, i.e., where a particle sticks to the surface and thus increases the current level is about 40 to 80 pA, which is consistent with the sizes of particles injected.

Figure 5:
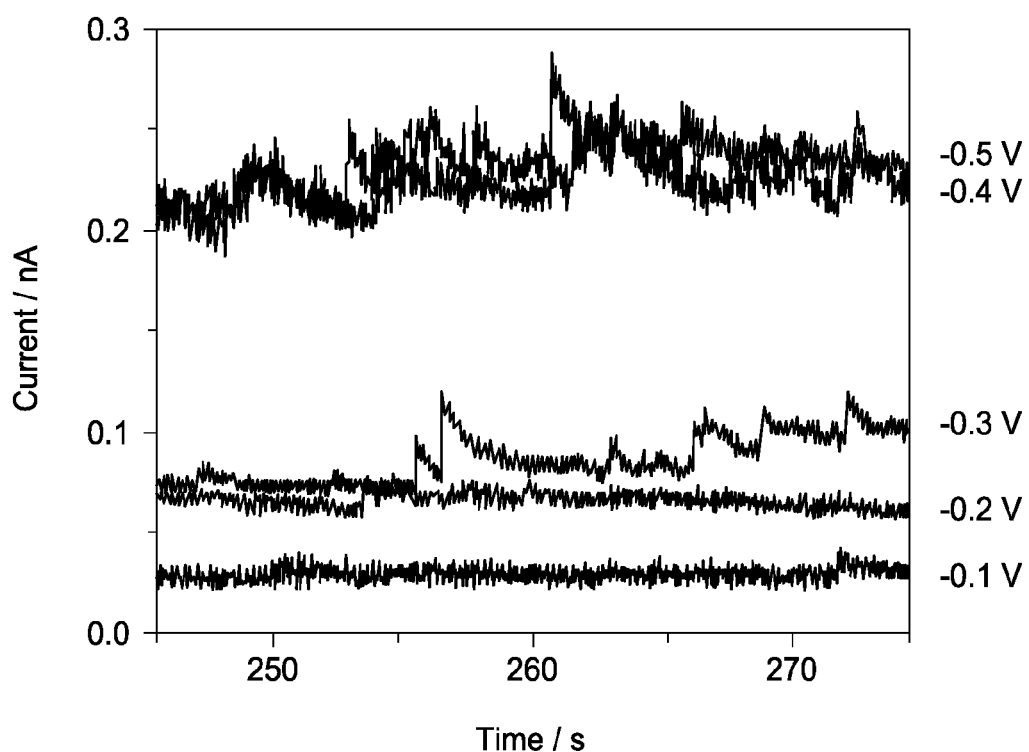
FIG. 5 is a graph that illustrates current transients at the carbon electrode at different applied potentials.

FIG. 5 is a graph that illustrates current transients at the carbon electrode at different applied potentials. The amplitude of the current spikes decreases with the positive shift of the electrode potential, which is in agreement with the steady-state current recorded at the platinum ultramicroelectrode. The proton concentration has large influence on the observed characteristic frequency and amplitude of the current spikes, which is shown in FIG. 3. The frequency of the collision was almost proportional to the particle concentration as seen in FIG. 6.

Figure 6:
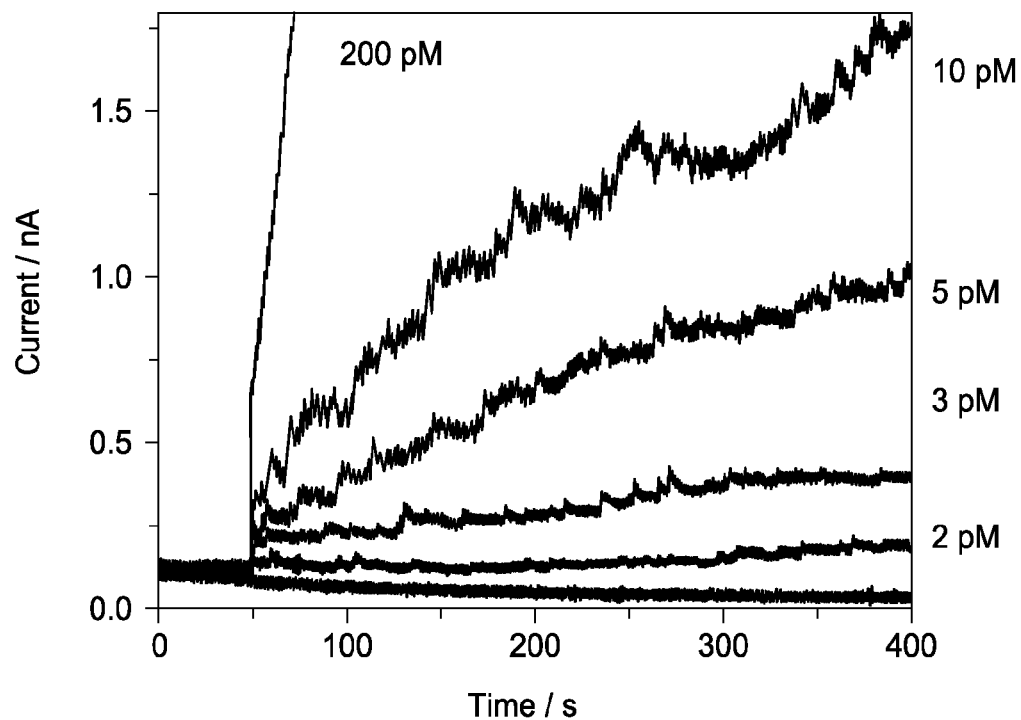
FIG. 6 is a graph of the current transients at the carbon fiber electrode at individual particle concentrations to relate the frequency of the collision to the particle concentration.
Figure 7:
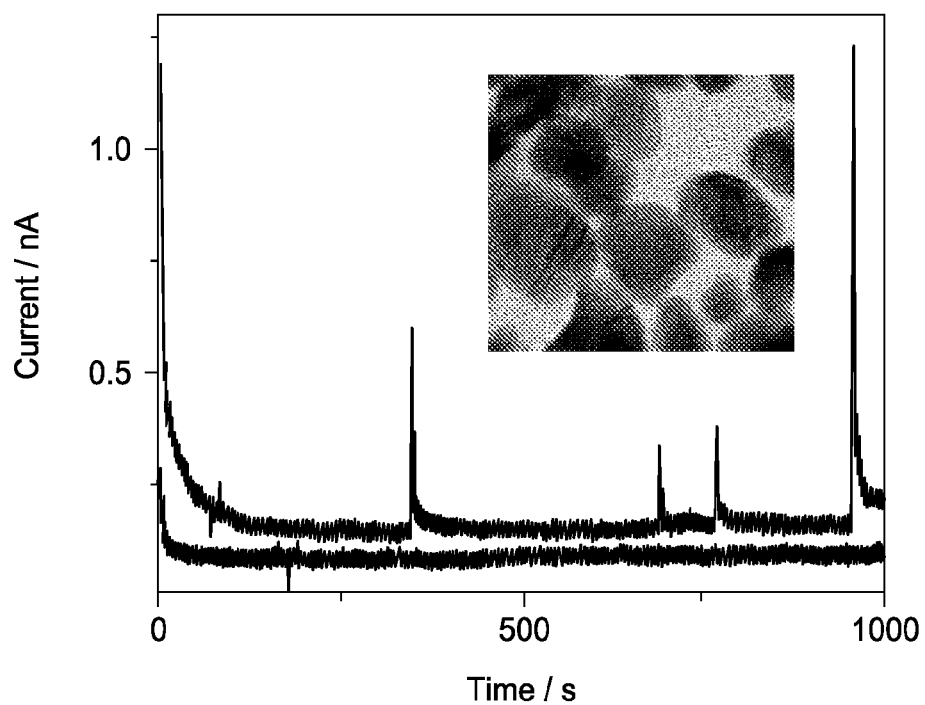
FIGS. 7 and 8 are graphs of the current amplitude resulting from various sized particles.
Figure 8:
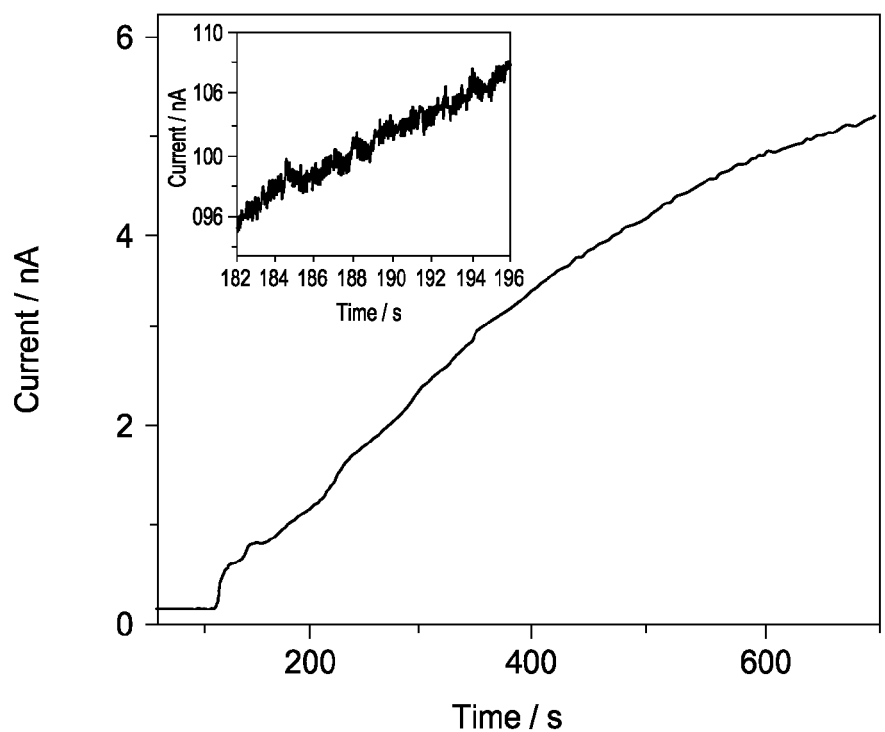

FIG. 6 is a graph of the current transient at the carbon fiber electrode in a 50 mM sodium dihydrogencitrate solution corresponding to five individual injections of platinum nanoparticles. The average frequency is about 0.02 per second per pM particle concentration at the carbon ultramicroelectrode used, which is very close to that estimated by equation 1 of 0.03 $s^{-1}$ $pM^{-1}$ particle concentration for an 8 µm carbon electrode. We assumed that the diffusion coefficient of particle is $1 \times 10^{-8}$ $cm^2/s$ and the particle concentration is about 1000-2000 times less than the concentration of $H_2PtCl_6$ used in synthesis, i.e., one particle has about 1000-2000 Pt atoms. The current amplitude varies with the size of particles injected, larger particles and bigger spikes, as shown in FIGS. 7 and 8 for particles bigger than about 8 nm and less than about 2 nm, respectively.

Particle collisions with the electrode typically give rise to three types of i-t responses, as shown in FIG. 4B. Each i-t profile is associated with individual single particle collisions. The characteristics of an individual i-t profile are affected by the particle size, the particle residence time and the interaction between particle and the electrode surface. In many cases, a particle leaves the electrode after its collision so the current increases but then returns to the background. This can be attributed to a repulsive interaction between the negatively charged particle and the negatively charged surface, this effect has been examined by setting the potential at even more negative values, where we observed fewer collisions. The reason that the current generated in each individual collision events varies, as illustrated by transients with characteristics denoted A, B, and C in FIG. 4B, is due to the nature of the collision (e.g. how closely a particle can approach to the electrode surface within a distance where electron tunneling is possible), the residence time and also to particle size effects. Deactivation of the particles, that is a loss of catalytic efficiency with time, is also a factor.

Figure 9A:
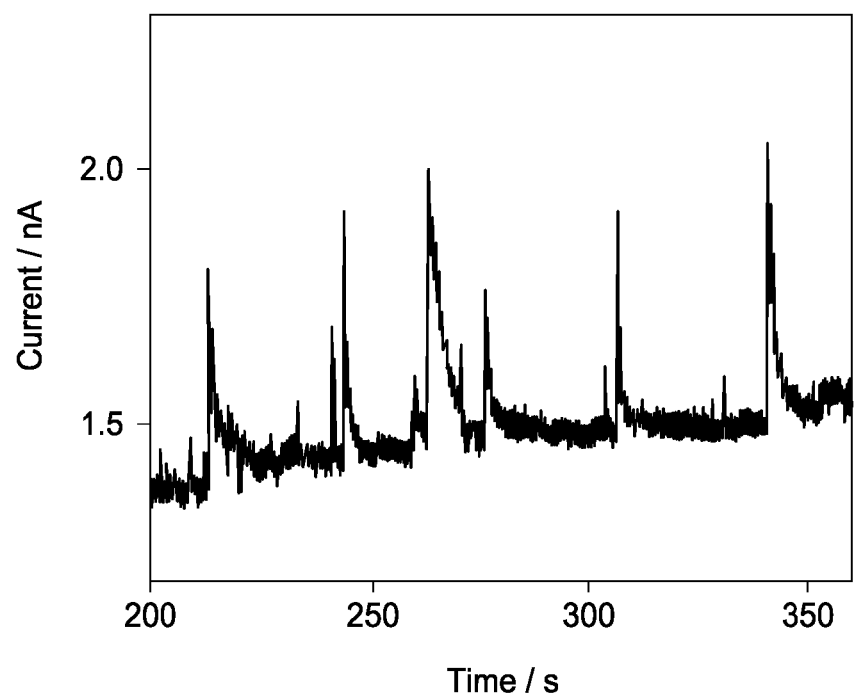
FIGS. 9A and 9B are graphs of the current transient at an ultramicroelectrode in the presence of platinum citrate nanoparticles.
Figure 9B:
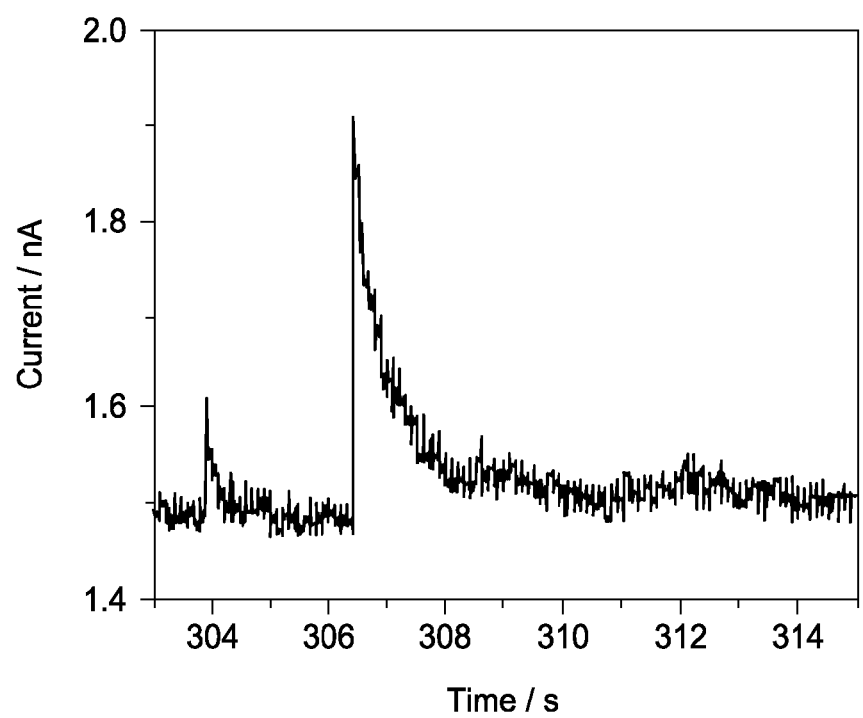
Figure 9C:
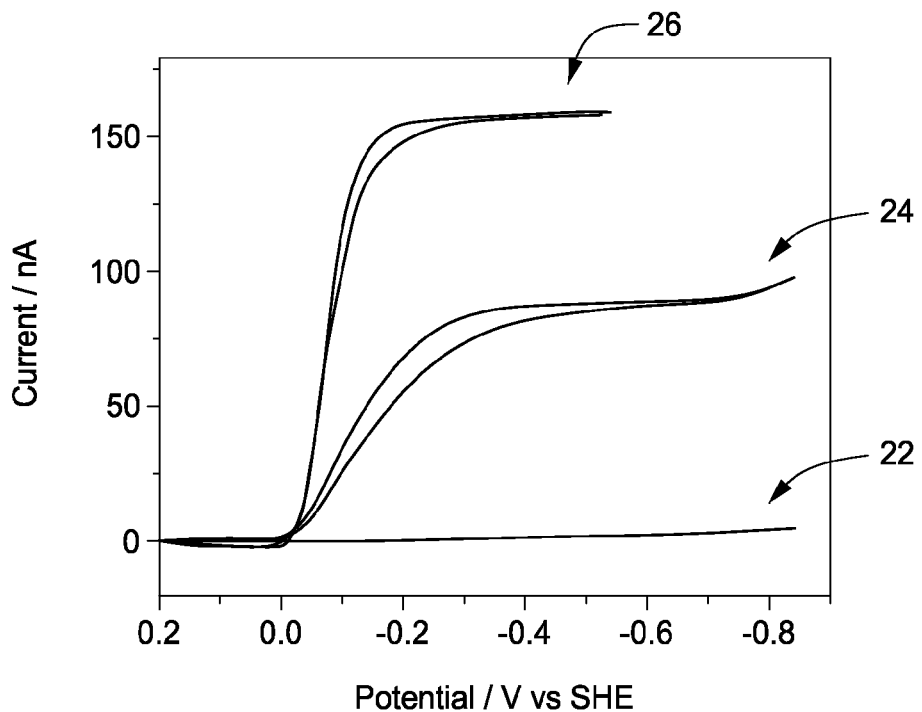
FIG. 9C is a cyclic voltammograms of carbon ultramicroelectrode curve 22 and platinum ultramicroelectrode.

FIGS. 9A and 9B are graphs of the current transient at an ultramicroelectrode. FIGS. 9A and 9B shows the typical shape of the representative spikes. The current maximum of individual spikes varies, signaling a very sensitive detection of the individual single particles, mostly related to the particle sizes, and the communication properties between the substrate surface and the particle surfaces. FIG. 9A is a graph of the current transient at a carbon ultramicroelectrode in 10 mM perchloric acid and 20 mM sodium perchlorate in the presence of platinum citrate nanoparticles. Particle concentration is about 25 pM. FIG. 9B is a zoom in of FIG. 9A. FIG. 9C is a cyclic voltammogram of carbon ultramicroelectrode curve 22 and platinum ultramicroelectrode in 50 mM sodium dihydrogencitrate curve 24 and 10 mM perchloric acid and 20 mM sodium perchlorate curve 26.

The advantage of using strong acid is that the kinetic process of deprotonation of weak acid can be ignored, as shown in FIG. 9C. However, when increasing proton concentration to 10 mM using strong acid, such as perchloric acid, the platinum nanoparticles are not stable due to the protonation of the carboxylic groups of citrate which stabilize the particles negatively. The stability of the particles can be also evidenced by recording the current transient in the presence of platinum citrate particles. Typically, right after injection of particles very abrupt spikes appear in the time frame of about less than 600 seconds, as shown in FIG. 3A. Interestingly, in this case there is no significant increase of the current after each spike, which clearly shows that the particles do not stick well to the surface, but give rise to catalytic current only for a relatively short time.

The current transients in the presence of large platinum nanoparticles, typically larger than 8 nm in diameter, were also taken. The particles are stabilized by oxalate. Only a few current spikes can be captured within the same time period and the same platinum concentration. The results are reasonable because both the particle concentration and the particle diffusion coefficient become smaller due to the larger particle sizes. However, the above described B and C types of collisions are not clearly observed, as shown in the current transients graph of FIG. 7.

Figure 10A:
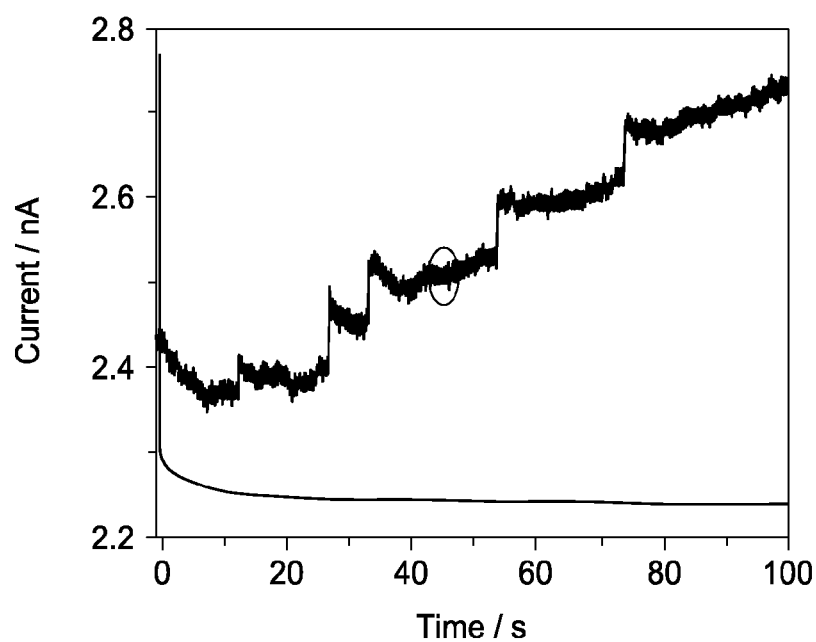
FIG. 10A is a graph of current transients in the presence of large platinum nanoparticles to illustrate B and C types of collisions.
Figure 10B:
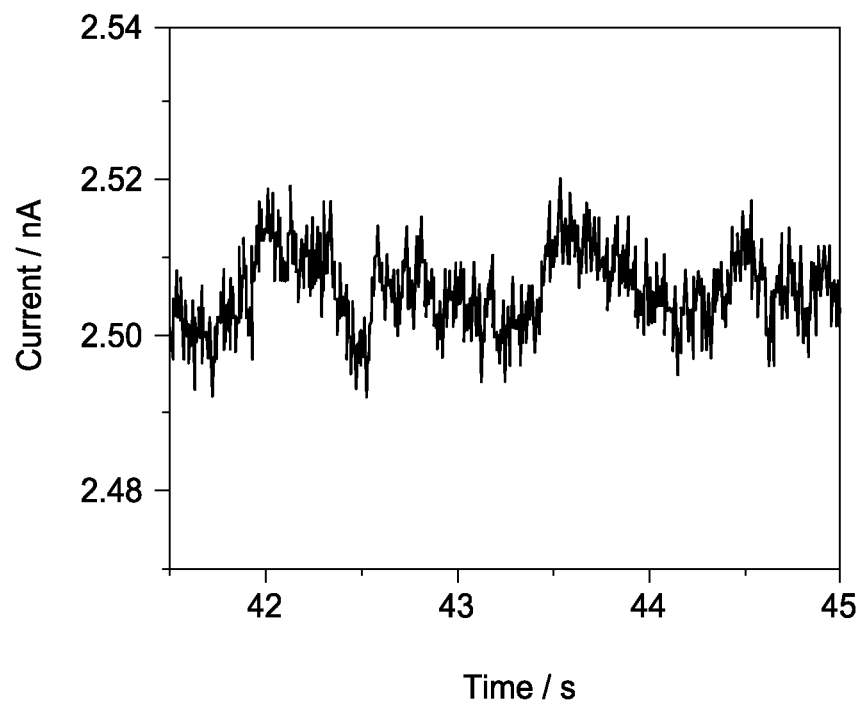
FIG. 10B is a graph illustrating the fluctuation shown in C type of collisions observed in proton reduction caused by smaller platinum particles in the preparation.

Single nanoparticle collision events have been examined using hydrogen peroxide as the indicator instead of proton, the skilled artisan will know that other compounds and indicators may be used, e.g., oxygen, for reduction reactions and hydrogen, methanol, and hydrazine for oxidations. In order to reduce the background current and promote binding of the particle to the electrode surface, a gold ultramicroelectrode (which is not catalytic for $H_2O_2$ reduction) was coated with a surface assembled monolayer of benzenedimethanethiol, which forms a stable monolayer capable of electron tunneling to solution species.[5] The terminal thiol group can strongly bind to the platinum particles. An instant increase of current is observed upon particle injection due to the proximity of immobilized platinum particles. In addition to the discrete steps in the i-t response, characteristic of sticky collisions, we also observed smaller current fluctuation with smaller amplitudes but with higher frequency. The frequency of these is about 2 orders of magnitude higher than that of the discrete current steps. The fluctuation shown in FIG. 10B is similar to the C type of collisions observed in proton reduction as shown in FIG. 4B and may be caused by smaller platinum particles in the preparation. The ultramicroelectrode or electrode may contain gold, carbon fiber microelectrodes and other materials like ITO. In addition, the indicators species may be a proton, hydrogen peroxide, oxygen or other materials known to the skilled artisan.

The present invention provides a novel method of observing single particle collision events with an ultramicroelectrode. A single event is characterized by the current generated through the particle-catalyzed reaction of an indicator present in solution. Since the indicator can be selected to have a high concentration and a high diffusion coefficient, large amplification occurs. Every collision produces a unique i-t profile that can be correlated to the particle size, the particle residence time, and the particle interaction with the electrode surface. By modifying the particle concentration, particle size (e.g. platinum citrate nanoparticles vs platinum dendrimer nanoparticles), applied substrate potential, and the concentration of the indicator, it should be possible to use the i-t profiles to obtain information about the indicator reaction at a single particle. In comparison to amplifying optical, conductivity and mass signals using nanoparticles,[6,7] the catalytic current amplification the present invention allows observation of single particle collision events and through the i-t curves, the study of electrochemical kinetics at the single particle level. Moreover, it might be useful in determining particle size distributions and as a very sensitive electroanalytical method, perhaps to the single binding event level.

The platinum nanoparticle solution was prepared by combining 60 mL of a 2 mM aqueous $H_2PtCl_6$ solution was mixed with 3 mL of 50 mM aqueous sodium citrate solution, then under vigorous stirring, 7 mL 120 mM aqueous $NaBH_4$ solution was added dropwisely. The solution was kept stirring for another half hour.

Metal nanoparticles (MNPs) of various sizes ranging from subnanometer to a few nanometers are of interest because of their large surface to volume ratio, size dependent optical properties, and high density of surface defects, these particles show unusual physical and chemical properties. The skilled artisan will recognize that other nanoparticle solutions may similarly be prepared, e.g., platinum, palladium, copper, silver, ruthenium, iron, aluminum, nickel, tin and gold as well as nonmetals, like carbon and tin oxide. The choice of the particle material depends on the electrode reaction that will be catalyzed. For example, the nanoparticles can comprise at least 50, 100, 300, 1000, or 3000 atoms of the element. For example, the nanoparticles can comprise at least 10,000; 30,000; 100,000; 300,000, or 1,000,000 atoms of the element. In certain embodiments, the nanoparticle comprises at least one of elemental carbon, graphite, carbon black, carbon nanotubes, and fullerenes. For example, the nanoparticles can include at least 100 atoms of an element selected from gold, platinum, palladium, rhodium, carbon, and copper. The nanoparticles do not have to be purely elemental (e.g., pure platinum) and may include alloys, oxides, and compounds, as well as core-shell type structures. In various embodiments, the nanoparticles may not be homogenous. In some embodiments, nanoparticles with differing compositions can be used simultaneously.

In electrochemical studies, MNPs are usually immobilized at an inert supporting material to form an electrode and their effect in electrocatalytic reactions, such as proton or oxygen reduction is probed. In characterizing the electrocatalytic effect of MNPs, the homogeneity of MNP size and shape plays a complicated role, as does their surface coverage on the supporting materials. One usually sees an average effect, and relating the activity to MNP properties is complicated by the effect of the surface coverage and total area, as well as the interaction of particle with support material. Thus there has been disagreement about the effect of particle size on electrocatalytic behavior. Generally, the characterization of electrodes at the single nanoparticle level has been limited in the art with numerous challenges with relatively few experimental studies.

It has also been proposed that nanoelectrodes or MNP electrodes would find applications ranging from single-molecule detection to real-time imaging of cell exocytosis. The size of these electrodes is comparable to those of biological molecules and of ion channels in biological membranes. However, the skilled artisan recognizes that making electrodes at nanometer scale is still technologically challenging. Moreover at nm size the current generated at such electrodes is usually at pA levels, making measurements with good signal-to-noise levels challenging. A variety of analytical tools have been developed to determine MNP size and size distributions, e.g. electron microscopy, scanning probe microscopy, UV-visible spectroscopy, surface plasma resonance, mass spectrometry, dynamic light scattering, and X-ray absorption spectroscopy (XRD and EXAFS). For example, transmission electron microscopy (TEM) is commonly and widely used to precisely determine the size of MNPs of a few nm in diameter by casting on a carbon grid support. The present invention provides an electrochemical method that is able to screen the MNP sizes in a liquid solution, and also provide a platform for the study of the kinetics of electrocataylysis at single MNPs.

Figure 11A:
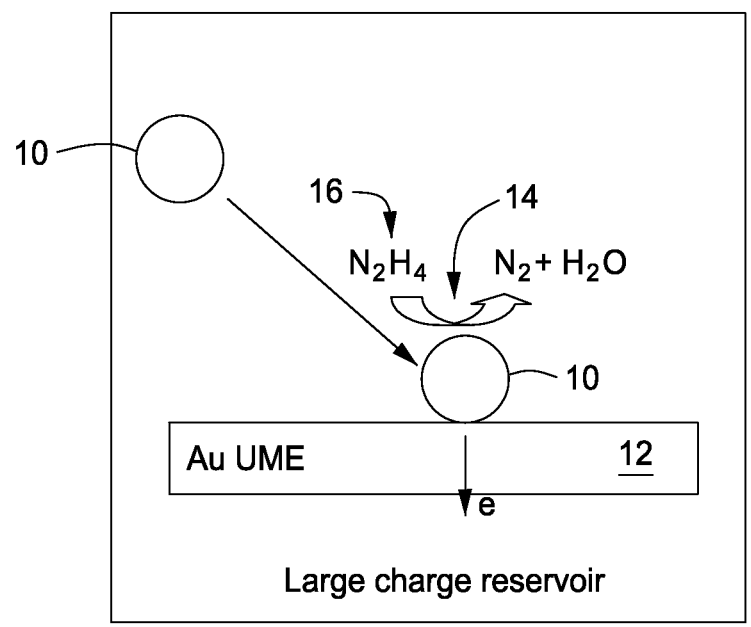
FIG. 11 is a schematic of another embodiment of the platinum nanoparticle collision event.

Briefly, a heterogeneous electron transfer reaction is selected that occurs sluggishly at a given detector electrode material, e.g. C, but takes place at the MNPs when they collide and stick at the electrode. Once the MNP is in contact with the detector electrode, electrons flow into or out of the MNP, maintaining the catalytic reactions at the MNP surface. FIG. 11A is a schematic of the platinum nanoparticle collision event for a single nanoparticle collision at the Au UME surface, the reaction is switched on when the particle is in contact with the detection electrode. The limiting current generated at a single spherical MNP in contact with a planar electrode is given by:

$$I = 4\pi(\ln 2)nFDCr \quad (3)$$

where D is the diffusion coefficient of reactants at concentration of C, and r is the radius of a single MNP. This equation is different from that for a spherical UME by the ln2 term, which accounts for blocking of the diffusion path to the MNP by the supporting planar surface.

Clearly, the particle size, or radius, is proportional to the catalytic current recorded at a given concentration of the reactants, assuming that D is kept constant in a certain concentration ranges of reactants and supporting electrolytes, which are mostly less than 100 mM.

To observe single MNP collisions, the first step is to amplify the current by selecting a catalytic reaction. The reaction rate at the MNP should first be significantly faster than that at the substrate within a certain potential range, e.g. proton reduction at Pt vs. C. Secondly, the catalytic reaction should occur under mass transport controlled conditions with negligible kinetic influence, where the current is proportional to the size of a single MNP, i.e., equation (3) applies. Since the heterogeneous kinetics of electrocatalysis at MNPs may be a function of their geometry and the capping agent, it is useful to minimize these effects by biasing the electrode at a potential where the diffusion limited current at the MNP is always maintained. Finally, the reactant should be at a high concentration and have a large diffusion coefficient so that a large enough current, well above the detection limit, i.e., of the order of tens of pA or more, is obtained In addition to proton reduction, reactions such as oxygen reduction, methanol and formic acid oxidation, oxidation or reduction of hydrogen peroxide, and hydrazine oxidation at Pt, Au, and C microelectrodes show potential differences in their electrocatalytic response at these electrodes. However, the current for oxygen reduction is limited by its low solubility in water, and the oxidation of small organic molecules, such as methanol and formic acid, leads to poisoning of the surface by adsorbed intermediates, like CO, which limits and causes instability of the oxidation current. The use of $H_2O_2$ is perturbed by the heterogeneous catalytic decomposition of hydrogen peroxide and gas bubbles are generated when Pt MNPs are injected into a hydrogen peroxide test solution. Hydrazine oxidation and proton reduction show distinguishable catalytic behavior among Pt, Au and C electrodes and yield reproducible responses in certain pH regions.

Figure 11B:
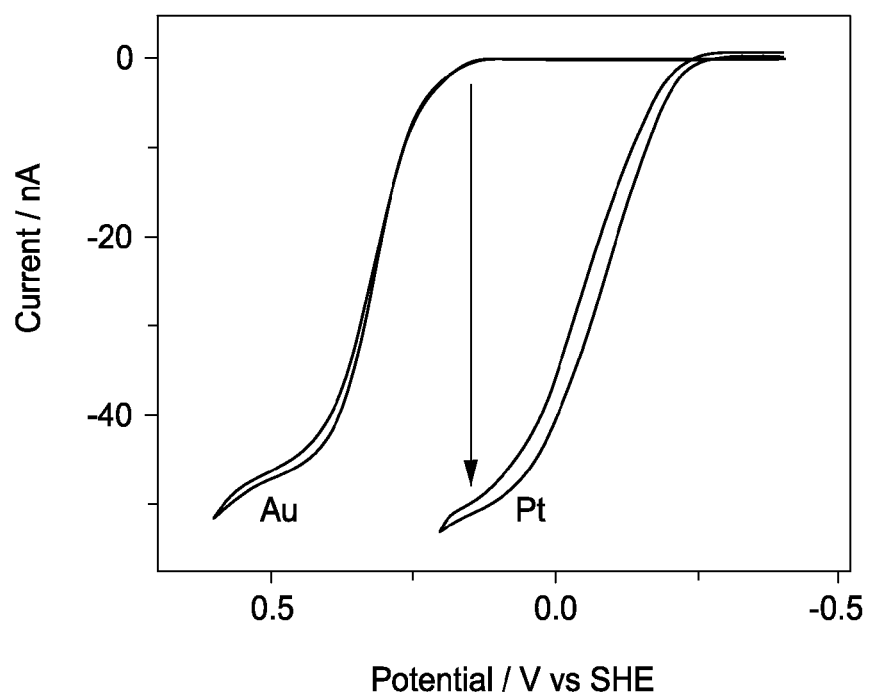

FIG. 11B is a graph of the current amplification tuning the hydrazine oxidation rate between Au and Pt UMEs where the scan rate is 50 mV/s and the electrolyte is 10 mM hydrazine and 50 mM PBS buffer with a pH of about 7.5. FIG. 11B as an example, shows that hydrazine oxidation gives rise to a steady-state limiting current at an Au UME at potentials above 0.4 V in a pH 7.5 phosphate buffer, while the potential for oxidation is shifted by about −0.5 V at a Pt UME. Such a potential shift would lead to a potential window that is large enough to tune the reaction rate at Pt to be significantly larger than that at Au. The steady-state limiting current is about 50 nA for 10 mM hydrazine and 75 nA for 15 mM hydrazine at pH 7.5 at an UME with a radius of 5 μm.

Figure 11C:
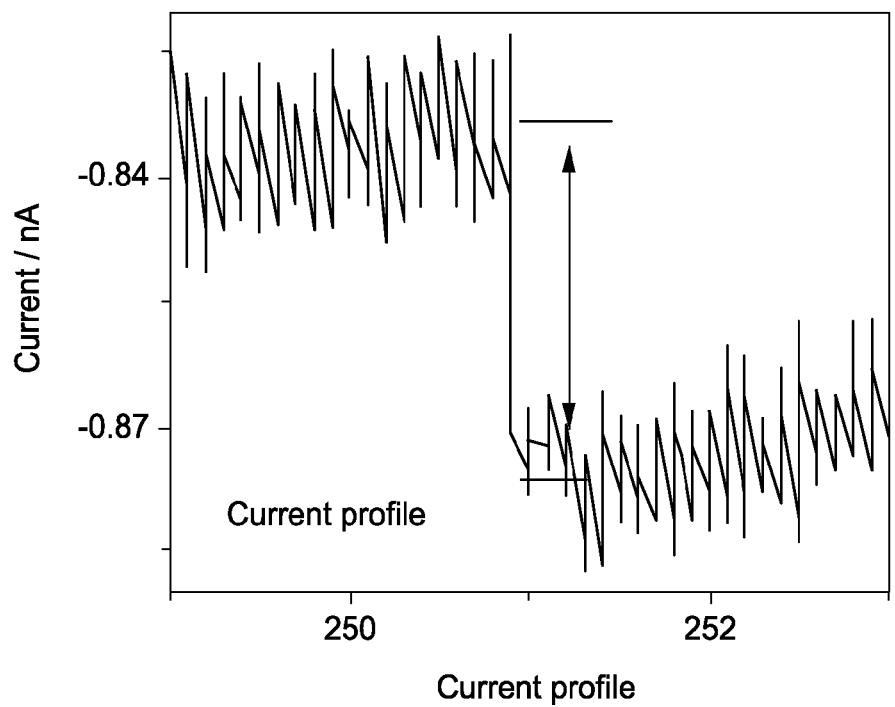

FIG. 11C is a graph of the representative current profile observed in a single nanoparticle collision event. The individual stepwise current profiles of FIG. 11C can be used to determine particle size, as described below. Such a current profile represents a single event of MNP collision and adhesion at the detector electrode before and after it switches on eletrocatalytic hydrazine oxidation at the particle surface. The current profile resembles the ones recorded at UMEs, indicating that a steady-state current at this MNP has been achieved. To determine the particle size, the peak height is directly related to the limiting current obtained at a Pt UME for the same test electrolyte. To evaluate the particle size distribution, we controlled the particle collision frequency by injecting very dilute Pt colloidal solutions into the test solution containing hydrazine and PBS buffer electrolyte. The well-separated current profiles signaled individual single MNP collision events.

The Pt nanoparticle (Pt NP) solutions were prepared through reduction of Pt precursors, $H_2PtCl_6$ or $K_2PtCl_4$ by sodium borohydride ($NaBH_4$) in the presence of sodium citrate. Briefly, 40 mL 2 mM $H_2PtCl_6$ (99.9%, Alfa Alsar) was mixed with 28 mg sodium citrate (99+%, Aldrich), followed by drop-wise addition of fresh sodium borohydride solution (99%, Aldrich) under vigorously magnetic stirring. The concentration of sodium borohydride was varied from 56 to 500 mM to control the particle size, and the solution was stirred for another 30 minutes. The nanoparticle solution prepared with $H_2PtCl_6$ had a relatively narrow size distribution around 3.2 to 5.3 nm diameter depending on the concentration of $NaBH_4$ injected as determined by TEM. A Pt NP solution with particle sizes distributed around 3.6 nm was mainly used in the described particle collisions. These colloidal solutions were stable for a few months in the synthesis solution. Reduction of $K_2PtCl_4$ by $NaBH_4$ led to very small NPs, around 1.3 nm diameter, or particle aggregates. The particle aggregates were star-shaped with sizes ranging from 13 to 25 nm. Both of these colloidal solutions were not stable. Pt particle solutions were also prepared through hydrogen reduction of $K_2PtCl_4$ in the presence of potassium oxalate. In this preparation, the Pt particles have better crystallites but the particle sizes are widely distributed between 5 to 16 nm. The skilled artisan will recognize that these synthesis routes may be modified or fine tuned to produce various results.

The NP concentration was usually calculated from the concentration of Pt precursor divided by the average number of Pt atoms that each particle contains. For example, a 3.6 nm Pt particle is assumed to contain about 1400 Pt atoms, therefore, the Pt particle concentration is 1400 times smaller than that of the Pt precursor. As confirmed by ICP-MS, the loss of Pt is negligible for the fresh prepared colloidal solution, e.g., less than 5% decrease of Pt concentration is possibly due to the adhesion of Pt particles to the magnetic stirring bar and the glass walls.

Particle size was determined by TEM. To space the Pt particles far apart at the TEM grids, the TEM grids were immersed overnight in Pt colloidal synthesis solutions diluted about 20 times with water, and then removed them from the colloidal solutions vertically and thoroughly rinsed with water. The carbon films were usually dry after this rinsing since the film was still sufficiently hydrophobic. This procedure was used to minimize the aggregation of the MNPs on the grid surface allowing the determination of particle aggregates or not. The TEM samples prepared by drop casting were used for comparison. TEM images were obtained from JEOL 2010F Transmission Electron Microscope (JEOL Ltd.). The TEM resolution for a point image was 0.194 nm. The TEM grids were carbon films supported on 200 mesh copper (Electron Microscope Sciences).

10 μm and 25 μm Au, Pt UMEs were prepared by melting the metallic wires into soft glass. After connection of the metal wire with a Ni—Cr lead with silver epoxy, the electrode was polished with 0.3 μm alumina until a mirror surface was obtained. The projected surface area and the quality of UMEs were obtained from voltammetry of ferrocene methanol oxidation in an aqueous solution. Before each use, the electrode was repolished with 0.3 and 0.05 μm $Al_2O_3$ powder.

The 1-hexadecanethiol (C16SH) and 16-mercaptohexadecanoic acid (HSC15COOH) self-assembled monolayers (SAMs) were prepared by immersing the clean Au electrodes into ethanol solutions containing about 1 mM of C16SH or HSC15COOH for different time periods, as discussed below. The electrodes were then thoroughly rinsed with ethanol, acetone and water.

Cyclic voltammetry and chronoamperometry were performed with a three electrode cell containing about 50 mL electrolyte (CH Instruments, Austin, Tex., Model 660). A carbon rod was used as the counter electrode, and a stainless steel wire coated with polypyrrole was used as the reference electrode. The electrode potential was calibrated by a standard Ag/AgCl reference electrode and rescaled to yield potentials vs. the standard hydrogen electrode (SHE). The electrochemical cell was maintained in a Faraday cage and the current transients were usually recorded with about 10 ms resolution. Before injection of the Pt colloidal solution, the electrode was subjected to a few potential cycles to clean the surface and then held at the potential where the background current was less than 300 pA. Noise would appear when the Faraday cage was opened for MNP injection. After closing the cage the cell was maintained in an Ar atmosphere. The currents generated by MNP collisions could be easily distinguished from the background noise at the amplification levels employed when the Faraday cage door was closed.

The current was recorded vs. time before and after the Pt colloidal solution was injected. The colloidal solution was injected into the test electrolyte while the solution was bubbled with Ar for about 10 seconds. This procedure quickly distributed the Pt NPs uniformly in the whole test electrolyte, but producing higher noise levels during this period. Generally, hydrazine oxidation and proton reduction were used as the indicator reactions for current amplification at Pt NPs.

Figure 12A:
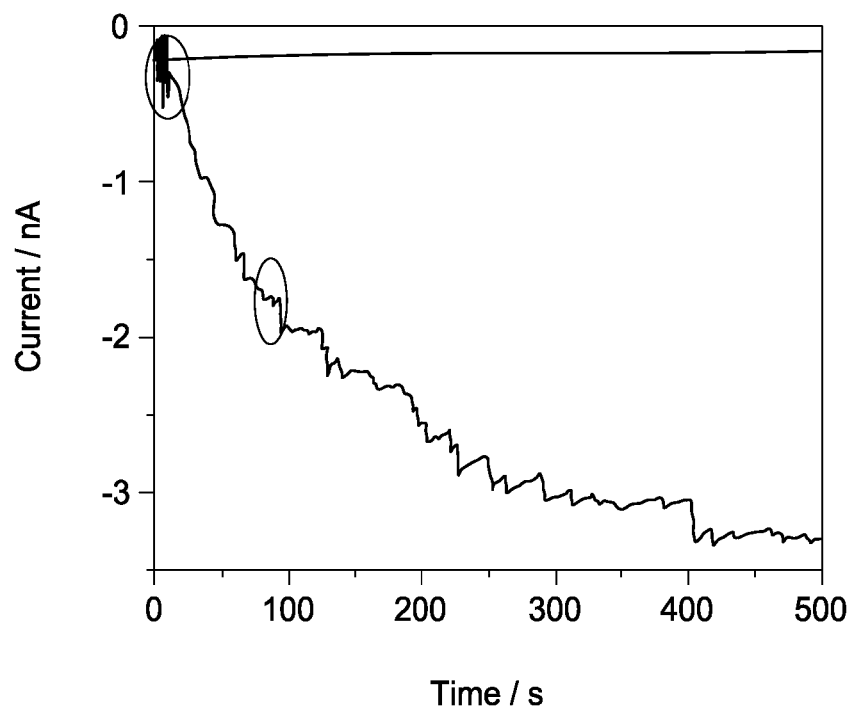
FIGS. 12A, 12B and 12C are graphs that show a representative current-time curves.

FIG. 12 is a graph that shows a representative current-time curve recorded at an Au UME, held at a potential of 0.1 V after mechanical polishing and electrochemical cleaning. The background current was about 220 pA and was essentially constant, decaying very slowly with time (FIG. 12A, blue curve). The large noise observed from 5 to 15 seconds was caused by the opening and closing of the Faraday cage door while the Pt particle solution was injected. The current was slightly offset after that period, which might be due to one or a few particle collisions during this time period. Following this period the solution was maintained as vibration free as possible and the current monitored. As shown, it increased anodically in a stepwise fashion.

Figure 12B:
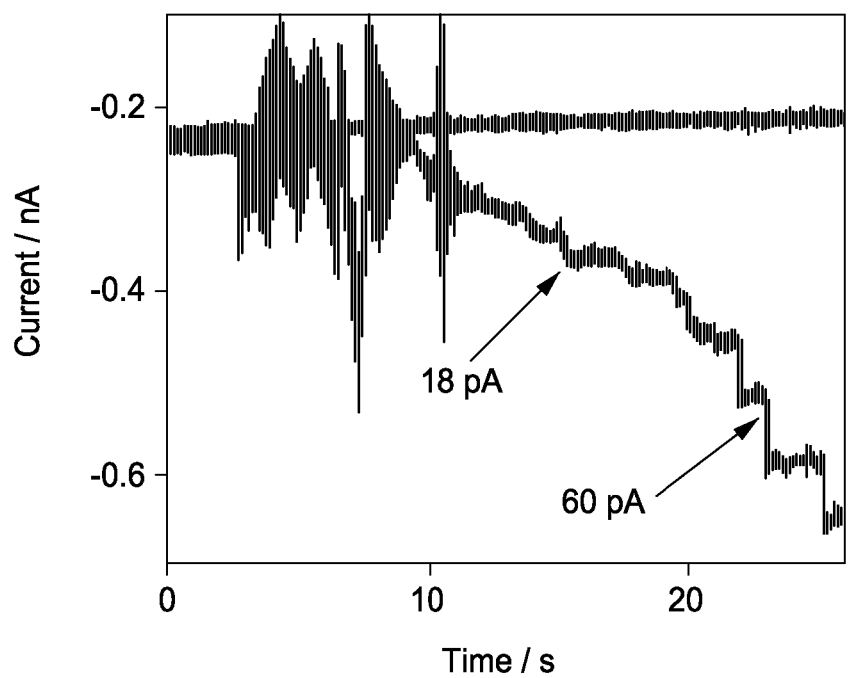
Figure 12C:
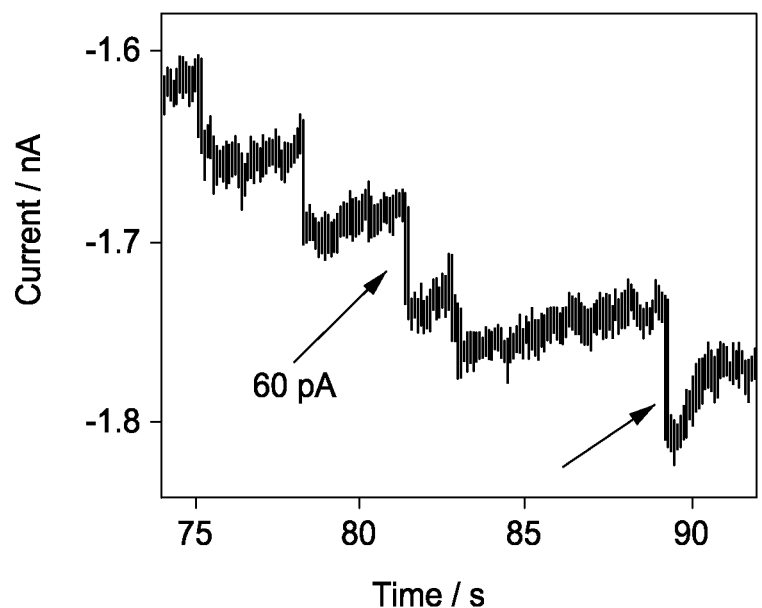

During the initial time period, shown in FIG. 12B, a few current steps of less than 20 pA in current amplitudes appeared. Note that these small current steps were also frequently observed later. Most of the current steps after this period were in the range of 40 to 65 pA. In each current step the current increased very rapidly and then remained at a steady state value. A few current steps showed longer transient times (FIG. 12, blue arrows), which may indicate microscopic details about the nature of the particle collision with the substrate (FIG. 12C). For example, although improbable at low concentrations, a particle might interact with another particle already on the surface. The rearrangement or fusion of two separate particles to become one unit would also lead to a decrease of practical surface area and thus the decrease of electrocatalytic current. The MNP might be deactivated by the adventitious impurities in solution. We have noted decays in the current generally at later recording times. There are clearly subtleties in the detailed shapes of the collision steps which need to be studied further, but are difficult to control.

Figure 13A:
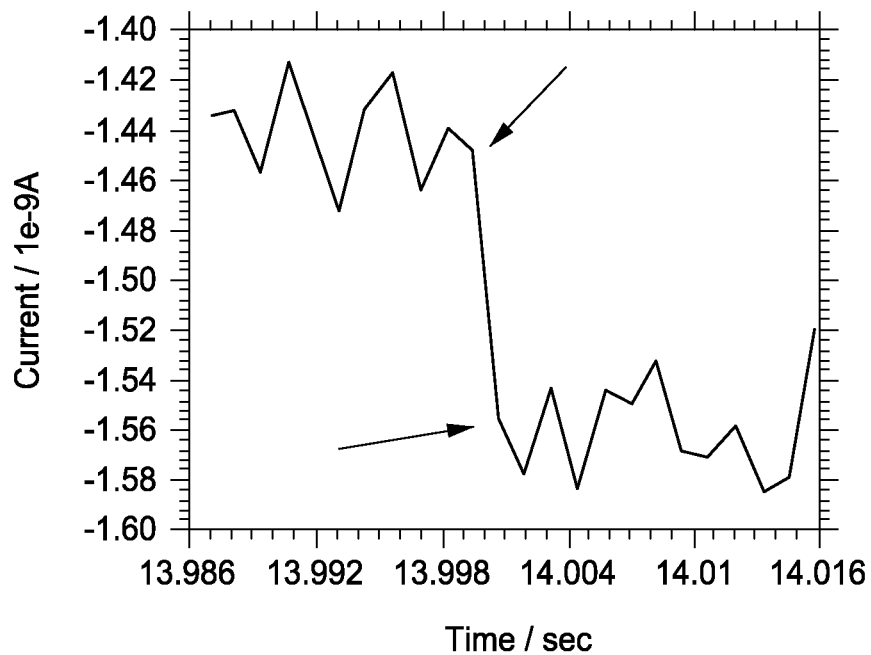
FIG. 13 shows two typical current transients recorded at 1 ms time resolution.
Figure 13B:
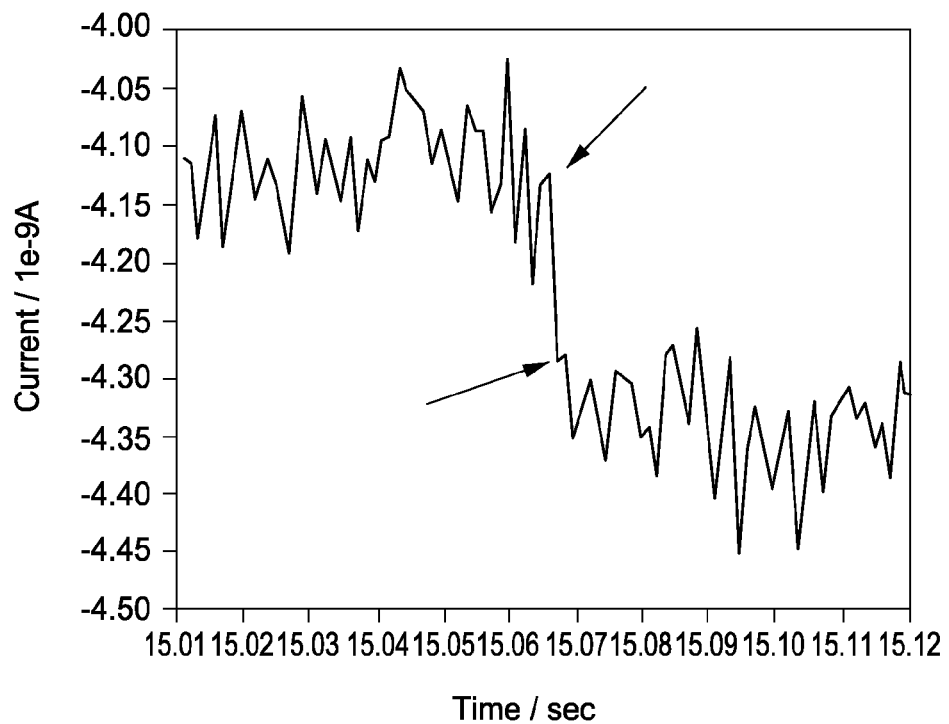

FIG. 13 shows two typical current transients recorded at 1 ms time resolution. FIG. 13 is a high resolution current transient for single Pt nanoparticle collisions. The current is switched at the limited resolution of our potentiostat which was set at 1 ms. The particle size is about 3.6 nm and 10 μm Au UME with 15 mM hydrazine and 50 mM PBS buffer at a pH of about 7.5. FIGS. 13A and 13B show two typical current transients recorded at 1 ms time resolution. The rise time is within 1 ms. Using a higher time-resolution oscilloscope (Tektronix 2440) directly connected to the potentiostat, we found that the rise time of the current steps was about 40 to 100 μs. This rise time probably also represents the instrumental limits of the potentiostat.

Figure 14A:
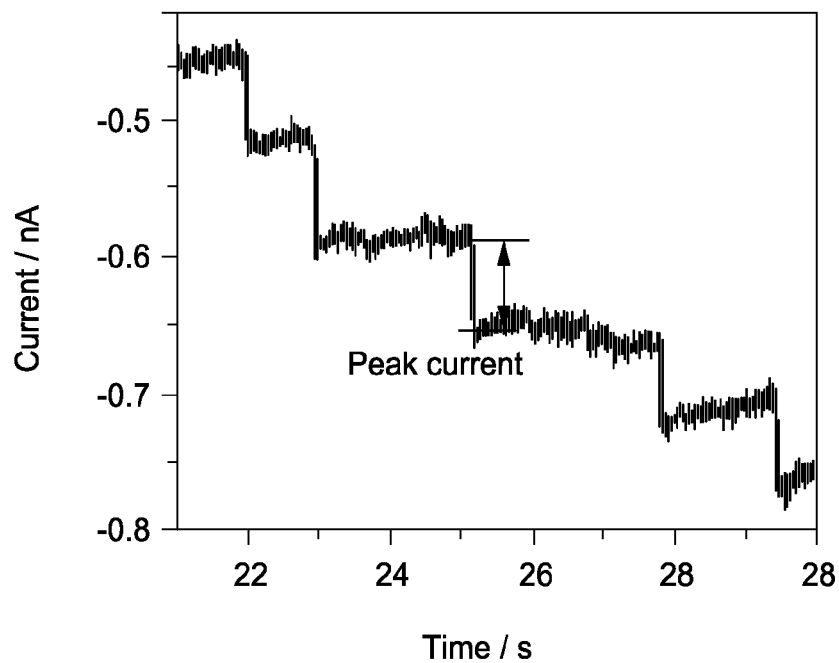
FIG. 14A is a graph of the current vs. time profile.
Figure 14B:
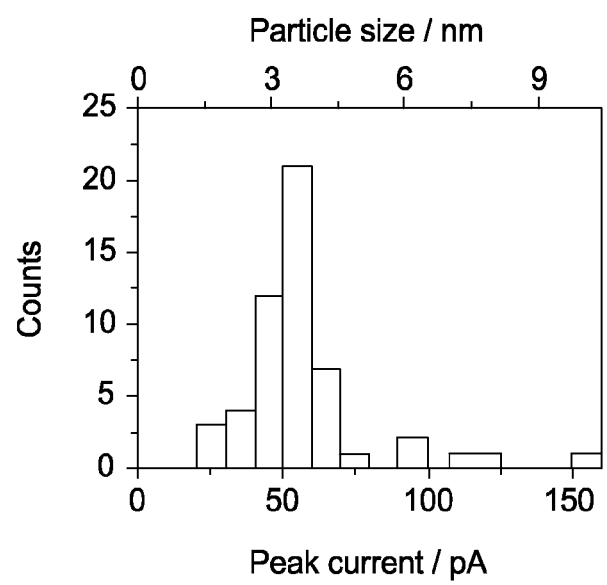
FIG. 14B is a plot of the statistic peak current vs. peak frequency.
Figure 14C:
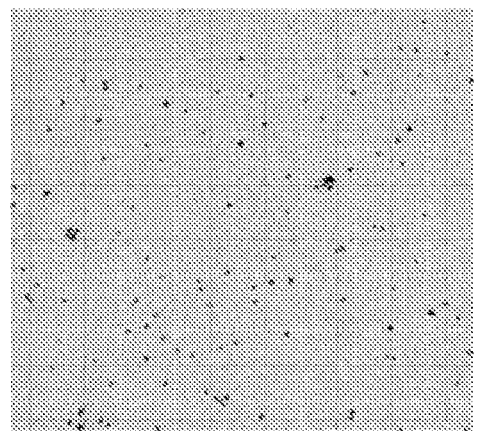
FIG. 14C is a TEM image of the sample and FIG. 14D is a size distribution plot of the corresponding Pt nanoparticles.
Figure 14D:
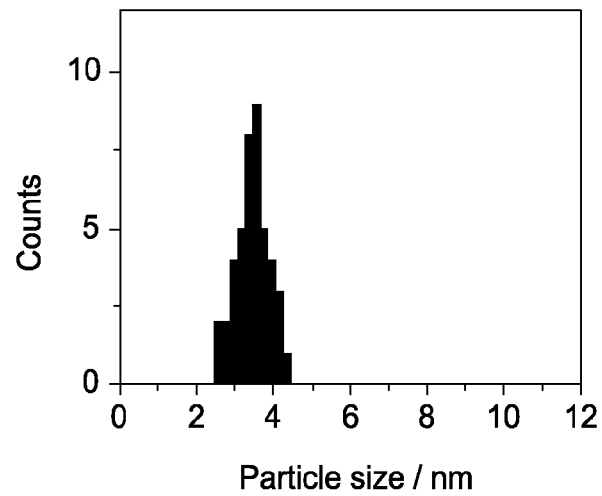

FIG. 14A is a graph of the current step graph for the current vs. time profile. FIG. 14B is a plot of the statistic peak current vs. peak frequency analyzed within 200 s. FIG. 14C is a TEM image and FIG. 14D is a size distribution plot of the corresponding Pt nanoparticles. FIG. 14A shows a typical current vs. time profile which contains several steps of about equal height (~60 pA). This leads to a particle radius via equation (3). For a larger number of steps one can plot the number of occurrences of a given peak current which indicates the main distribution between 40 and 65 pA with smaller numbers of larger peak currents around 100 and 160 pA (FIG. 14B). Since each current profile signals a single particle collision event, the distribution of the peak currents should reflect the distribution of the NP sizes. Indeed, it agrees well with the particle size distribution determined by TEM image FIG. 14C and distribution FIG. 14D). Note that these Pt NPs are also attached at the surface of TEM grids through particle random collisions, even though they are attached at the open circuit potential at the carbon surface. The size distribution of MNPs should represent the particles attached at the electrode surfaces in the collision experiments described above. The larger peak currents probably are caused by collisions of MNP aggregates.

Figure 15A:
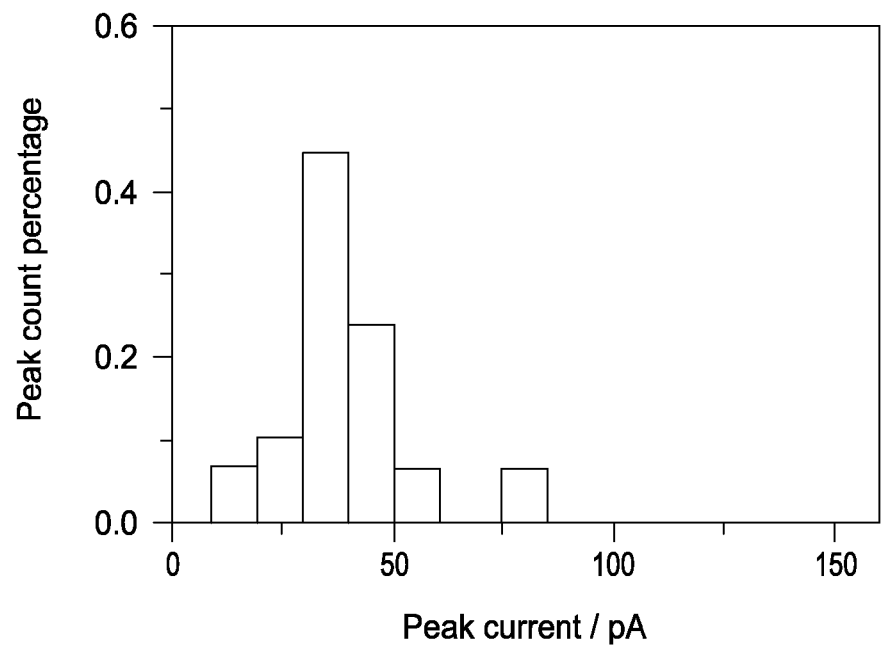
FIGS. 15A, 15B and 15C are plots of the peak current distribution shifts with the hydrazine concentration.
Figure 15B:
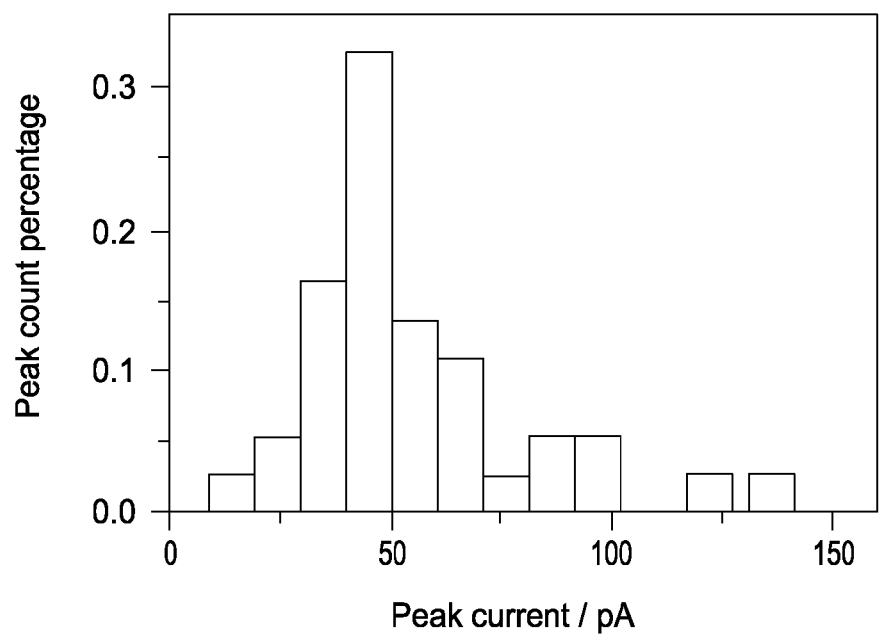
Figure 15C:
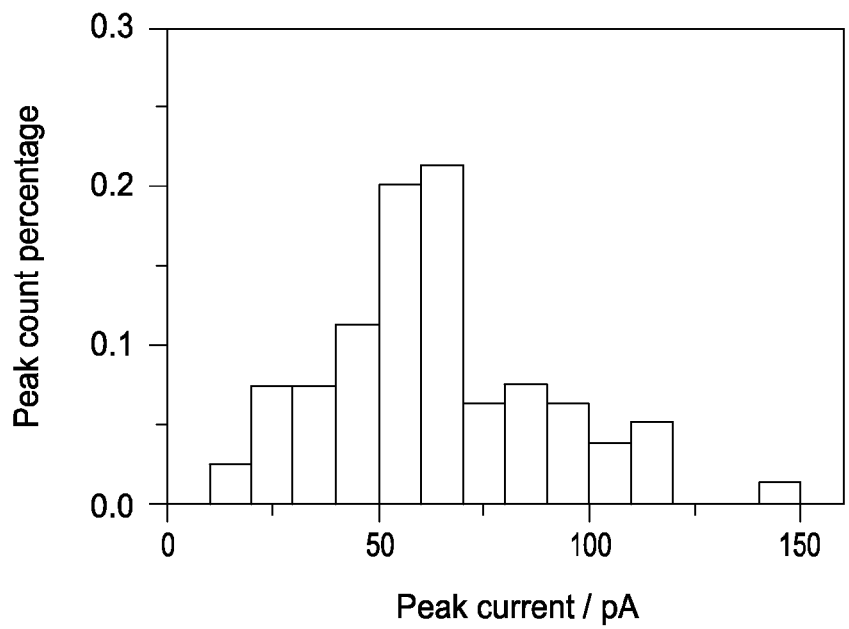
Figure 15D:
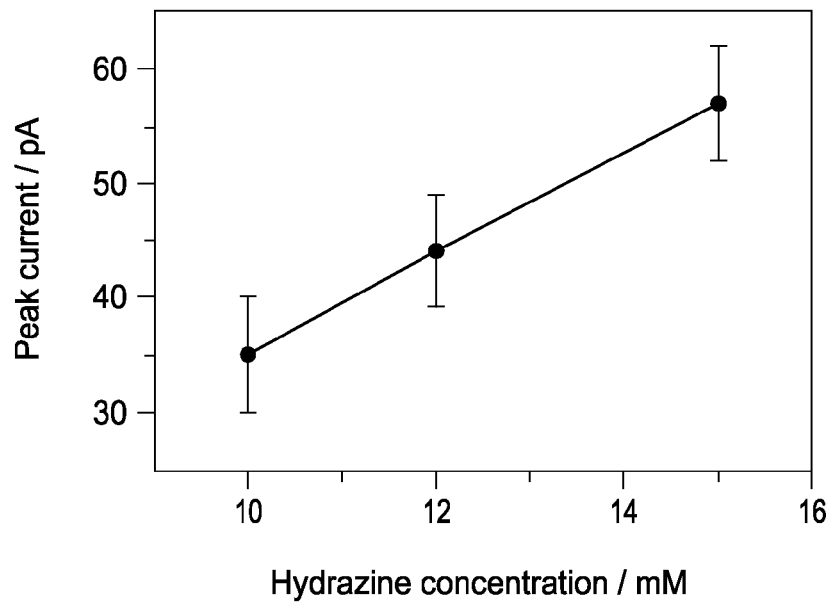
FIG. 15D is a plot of major peak current vs hydrazine concentration.

FIGS. 15A, 15B and 15C are plots of the peak current distribution shifts with the hydrazine concentration, and FIG. 15D is a plot of major peak current vs hydrazine concentration. Note that the shape of the distribution is slightly varied since the time scale for statistic analysis is different, usually longer time, more counts for large peaks.

The individual current profiles were shown to be due to single MNP collisions by carrying out studies under different conditions, e.g. hydrazine concentration, particle concentration, nature and area of the detection electrode (C and Au UMEs), and the particle sizes. When the hydrazine concentration was changed, the amplitude of the current step changed proportionally for the same colloidal Pt solution injected. Therefore, for a given concentration of hydrazine, we can directly evaluate the particle size distribution by the distribution of peak currents.

Figure 16A:
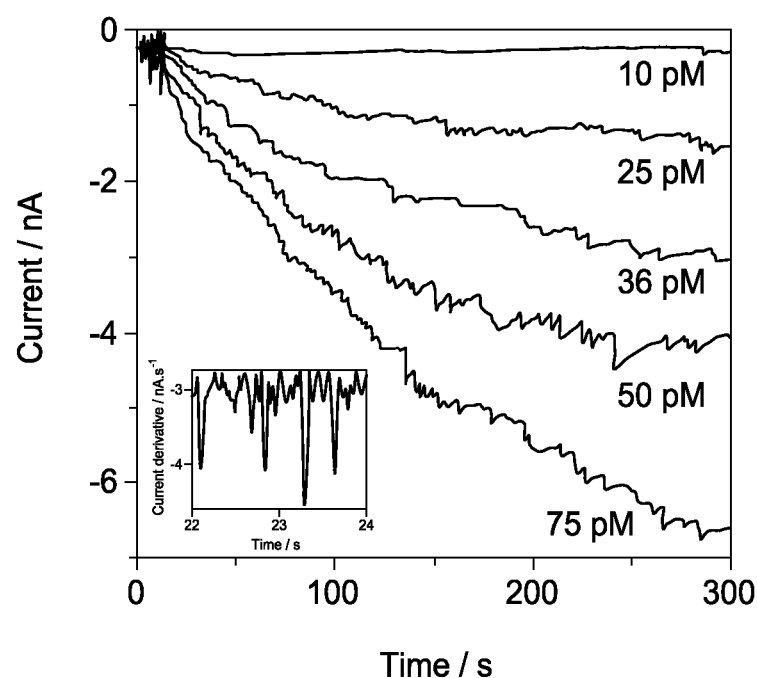
FIG. 16A is a plot of the current transients recorded at individual Pt particle concentrations and FIG. 16B is a plot of the correspondent first order derivatives.
Figure 16B:
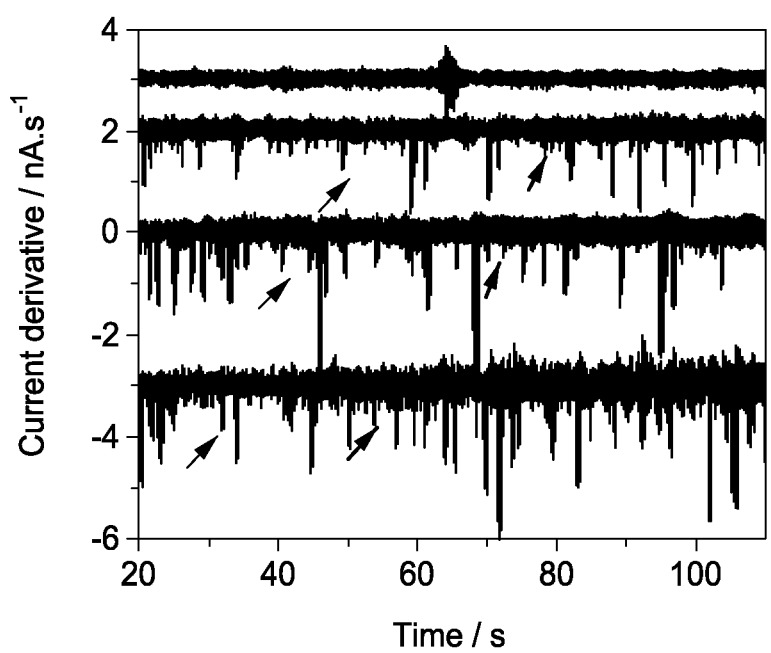

FIG. 16A is a plot of the current transients recorded at individual Pt particle concentrations and FIG. 16B is a plot of the correspondent first order derivatives. The bronze curve in FIG. 16B is from the current transient recorded in the absence of MNPs. The traces were offset from zero for clarity. The blue arrows point to the spikes which give rise to current steps above 20 pA and the red arrows to the current steps less than 20 pA. The particle size is about 3.6 nm, and 10 μm Au UME, with a solution of 15 mM hydrazine and 50 mM PBS buffer with a pH of about 7.5. With increasing concentration of Pt NPs, the peak frequency was increased while the amplitude of the peak currents remained unaltered as seen in FIG. 16. The collision frequency was increased about twice when 25 μm diameter Au UMEs were used instead of 10 μm Au UMEs.

The first order time derivative of the current was used to count steps and obtain the frequency of occurrence, as shown in FIG. 16B. Here, each spike represents a current step and thus a single event of particle collisions. The separation between individual spikes range from a few seconds to a few ms. The fluctuation in the frequency with time to observe spikes indicates that collisions of MNPs with the electrode from the bulk electrolyte are a random process. This collision process may also include some collisions of MNPs at the detector electrode which do not lead to particle adsorption, i.e., the particle residence time at the electrode may be varied from one particle to another.

The bronze curve in FIG. 16B shows the signal to noise level recorded in the absence of MNPs. The amplitude of the fluctuation is almost equally distributed in both upwards and downwards directions. The spikes having the amplitudes larger than the ones pointed by blue arrows are correspondent to the current steps which are bigger than 20 pA. These spikes are due to the MNPs which stick to the substrate after collisions. The frequency of these spikes is about 0.012 to 0.02 $pM^{-1}s^{-1}$ (i.e. for a 25 pM particle concentration, the frequency is about 0.4 $s^{-1}$ or an average time between collisions of about 2 seconds (see FIG. 16B, red curve)). The spikes pointed by the red arrows might be also due to collisions of MNPs. Since these collisions lead to current spikes rather than current steps, they are possibly correlated to the collisions of MNPs for a very short residence time at the detection electrodes.

The collision frequency can be determined by assuming that all MNPs collide then stick at the detector electrode at diffusion limited steady-state conditions, yielding a flux, J given by:

$$J=4D_pC_p/\pi a \qquad (4)$$

where Dp and Cp are the diffusion coefficient and concentration of Pt particles, and a is the radius of the UME. With a known particle concentration and radius of an Au UME, the observed collision frequency corresponds to a NP diffusion coefficient of $\sim 1\times10^{-8}$ cm$^2$/s. However the diffusion coefficient of Pt NPs in the range of 3 to 4 nm is estimated to be about $1\times10^{-7}$ cm$^2$/s based on the Stokes-Einstein relation for NP diffusion and other data.

In order for a current step to be observed, the particle has to stay in contact with the electrode surface for a certain time which is long enough to generate observable current. So what we observed is the sticking frequency instead of the collision frequency. The probability for particles to stick is thus about 1 to 10% of collisions in this experiment.

Whether or not the test electrolyte keeps the particles stable plays a very important role. The number of current steps per particle concentration was dramatically decreased when 10 mM sodium citrate was used as supporting electrolyte instead of 50 mM PBS. This is because the Pt particles are relatively stable in a citrate solution. The particles would remain favorably in the liquid phase, leading to low sticking probability. While in a PBS solution, the particles are not stable and tend to aggregate and precipitate, which makes them easier to stick at the surface after collisions. This also explains why we observed less and less occurrence of current steps with time. The surface modification of the detection electrodes may affect the particle sticking probability, but so far, we have not seen big differences, mostly within the same order of magnitude. We observed a slight increase in current steps when the potential of the detection electrode was set more and more positive, and a slight decrease when the Au surface was modified with negatively charged 3-mercaptopropionic acid.

It is worthy mentioning that the number of particles counted from TEM grits is much smaller than that calculated through equation 4. For a TEM sample grid immersed in a 25 µM Pt colloidal solution overnight one would expect to have more than one thousand particles per µm$^2$ estimated by equation 2 using a diffusion coefficient of $1\times10^{-7}$ cm$^2$/s. Instead, a variety of surface areas have less than 20 particles per 1 µm$^2$.

Figure 17A:
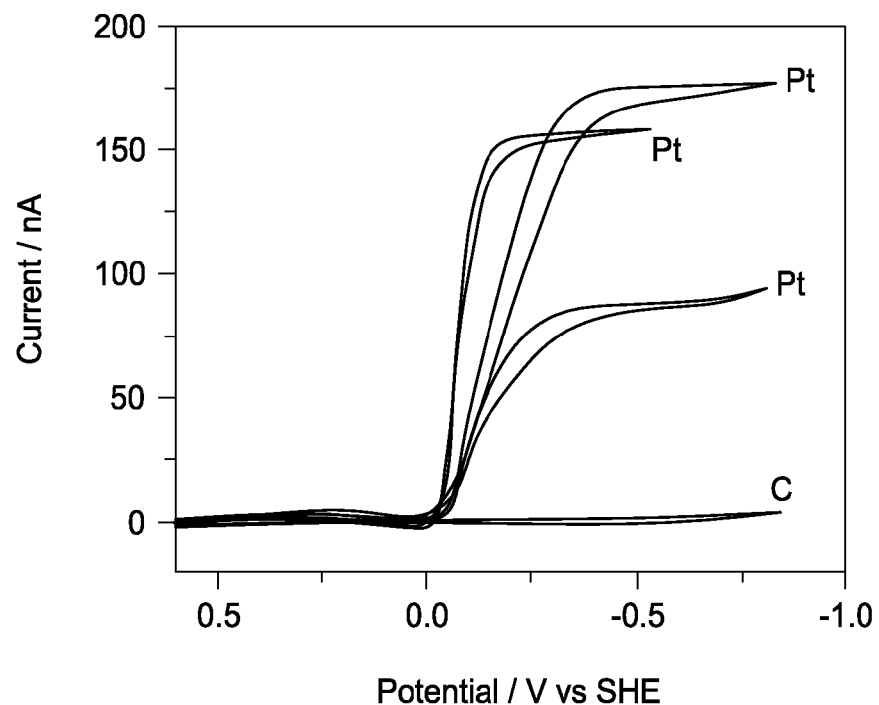
FIG. 17A is a cyclic voltammograms at Pt and C UMEs in 50 and 100 mM sodium dihydrogencitrate electrolytes and 10 mM perchloric acid electrolyte.
Figure 17B:
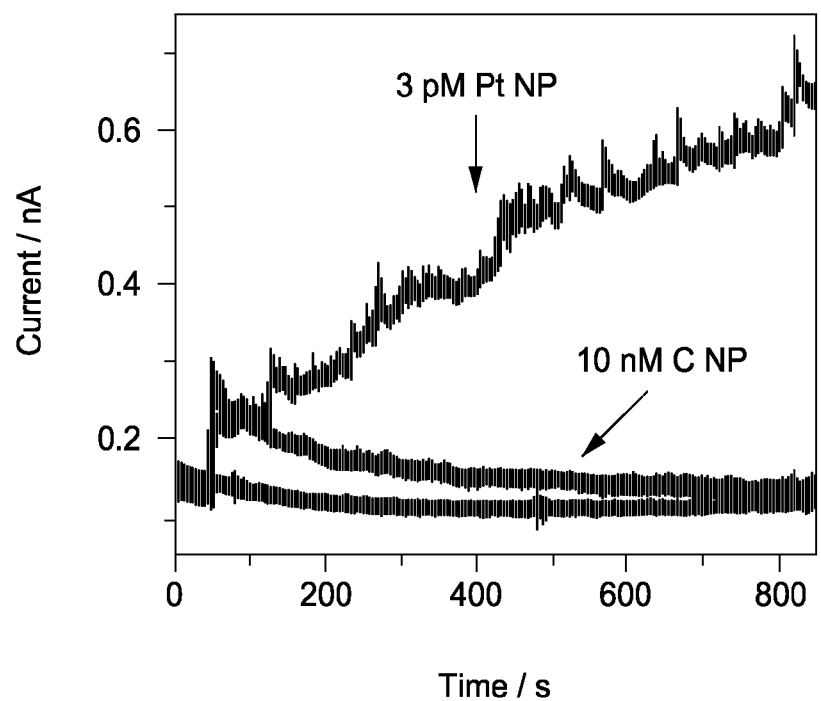
FIG. 17B is a graph of the current transients recorded before and after injection of C and Pt nanoparticle solutions.
Figure 17C:
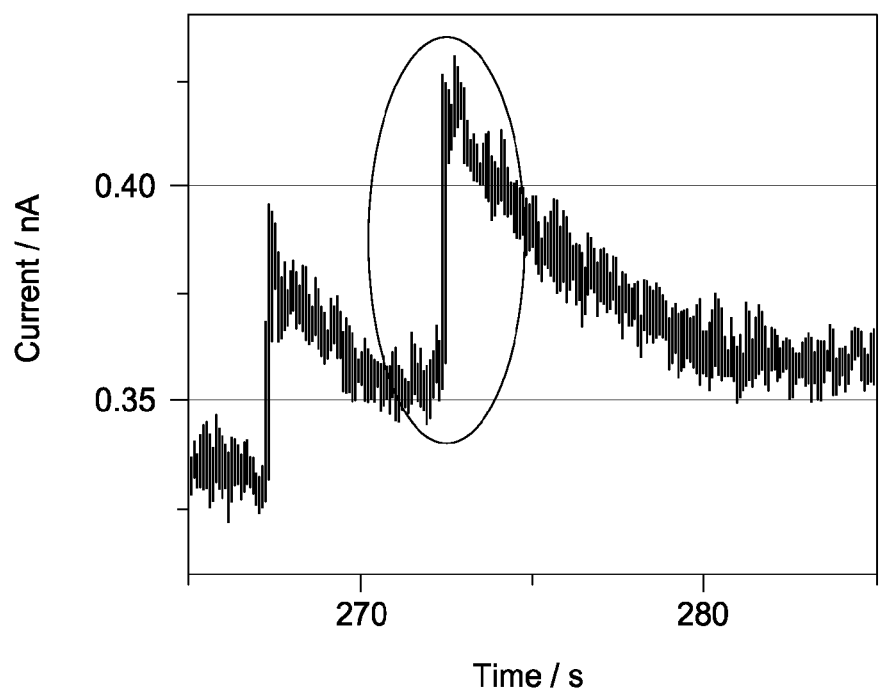
FIGS. 17C and 17D are enlargements of the individual current profiles.
Figure 17D:
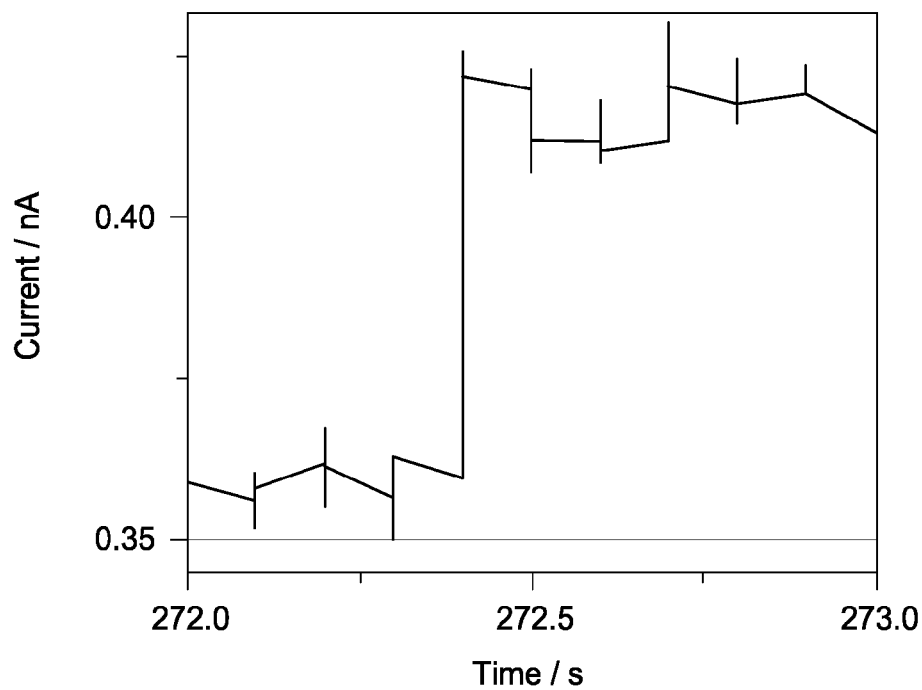

FIG. 17A is a cyclic voltammograms at Pt and C UMEs in 50 and 100 mM sodium dihydrogencitrate electrolytes (green and blue) and 10 mM perchloric acid electrolyte (red). 100 mV/s. FIG. 17B is a graph of the current transients recorded before (black) and after injection of C (red) and Pt (blue) nanoparticle solutions. FIGS. 17C and 17D are enlargements of the individual current profiles. The samples include 50 mM sodium dihydrogencitrate, with an electrode potential of −0.5 V, a Pt nanoparticle size of about 3.6 nm, Proton reduction at carbon electrodes occurs sluggishly and requires a high overpotential, while this reaction is rapid at Pt, as demonstrated by cyclic voltammograms at Pt and C UMEs in strong and weak acid electrolytes as seen in FIG. 17A. A steady-state diffusion limited current was observed in both HClO$_4$ and sodium dihydrogen citrate (NaH$_2$Cit). 50 mM NaH$_2$Cit is used as the proton source since Pt NPs are relatively stable in this environment, while they tend to aggregate in 5 mM HClO$_4$. The steady-state limiting current is about 70 nA at a 10 µm Pt UME. Injection of Pt colloidal solution to 100 mM NaH$_2$Cit or pure HClO$_4$ leads to aggregates. FIG. 17B shows the three current-time curves recorded at carbon fiber microelectrodes. No obvious current spikes were observed in either the background or when a solution of C NPs (instead of Pt NPs) was injected into the test electrolyte. When Pt NPs were injected, the overall current increased, superimposed with current spikes. These current spikes are similar to those observed in the case of hydrazine oxidation. However, the current did not maintain a constant steady state level for longer times, as observed with hydrazine oxidation. The current remained at the maximum value only for less than one second and then decayed slowly almost to the background level (e.g., see FIGS. 17C and 17D). Note that almost every current profile showed such a current decay. The peak currents are ranged from 30 to 80 pA, which correlate to the particle sizes ranging around 4 nm.

Figure 18A:
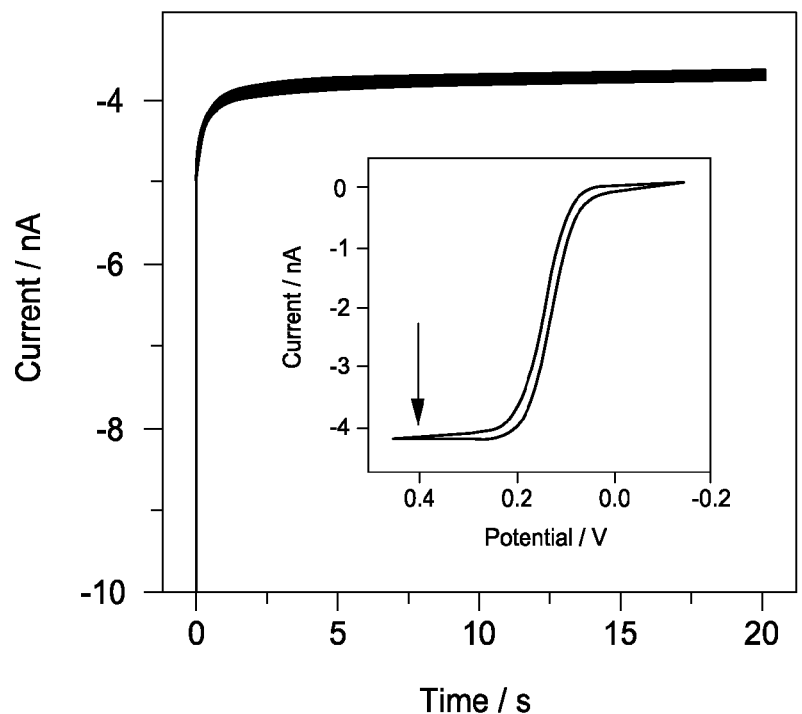
FIGS. 18A, 18B and 18C are images of current transients and cyclic voltammograms in various solutions.
Figure 18B:
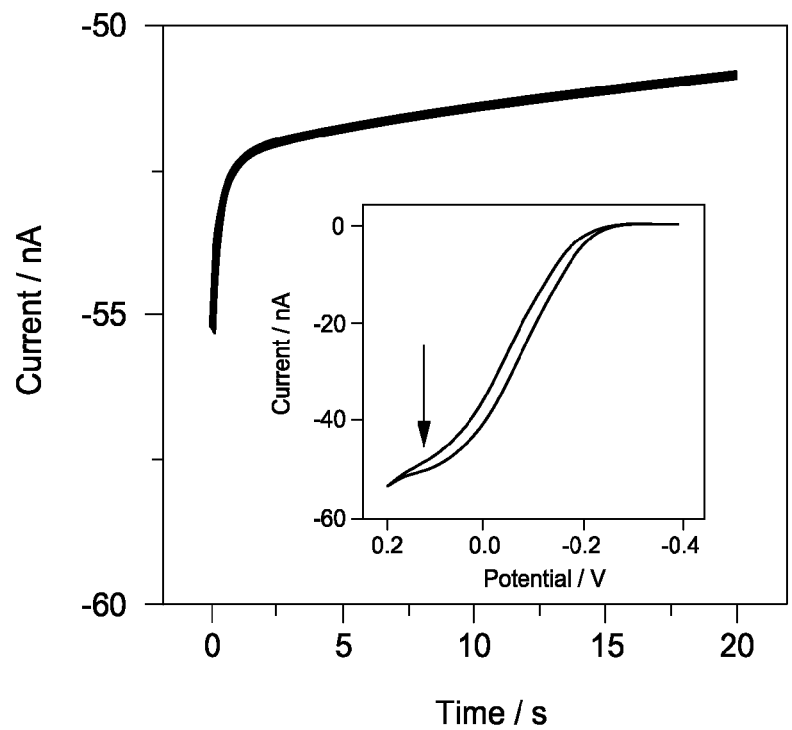
Figure 18C:
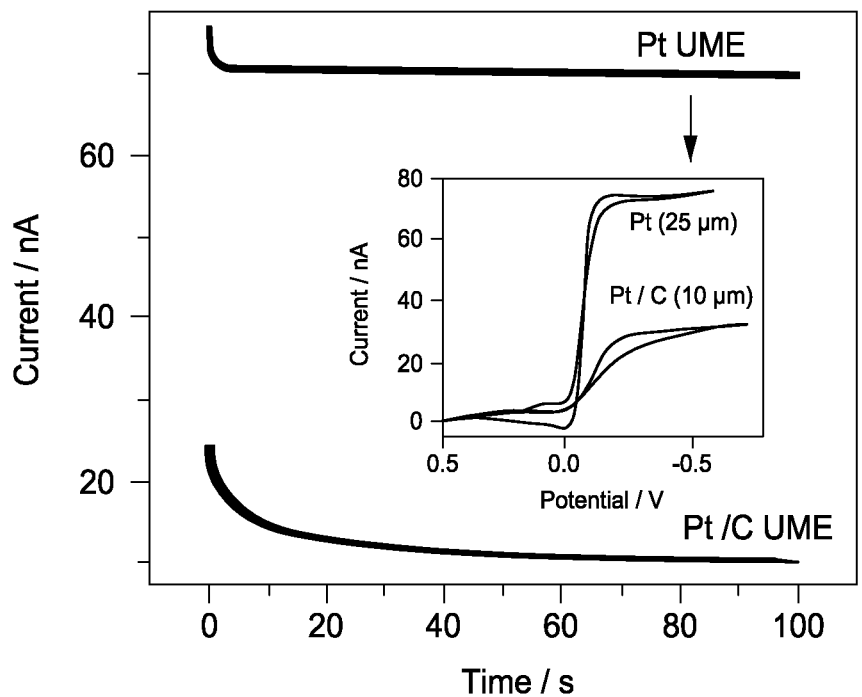

FIGS. 18A, 18B and 18C are images of current transients and cyclic voltammograms at Pt UMEs in FIG. 18A 3 mM Fc-methanol+0.1 M sodium perchlorate, FIG. 18B 12 mM hydrazine+50 mM PBS buffer, and FIG. 18C 2 mM perchloric acid+20 mM sodium percharate. The black arrows indicate the pulse potentials. Pt 10 µm diameter, FIG. 18C has a Pt 25 µm (black) diameter, and Pt deposited at carbon fiber, 8 µm in diameter (blue).

The decay of the current following a collision is more prominent with proton reduction than with hydrazine oxidation. The current transients at the Pt UMEs for proton reduction and hydrazine oxidation were compared to ferrocenemethanol oxidation. The current transient for Fc-methanol oxidation shows a negligible current decay after reaching the steady-state current within 20 ms (as seen in FIG. 18A). Hydrazine oxidation shows similar behavior as that of ferrocene-methanol (as seen in FIG. 18B), while proton reduction shows a little longer transient time, especially at the carbon electrode modified with Pt NPs (as seen in FIG. 18C). From 0.5 to 10 s, the current decayed about 6% for ferrocenemethanol, 3% for hydrazine, and 32% for proton (as seen in FIG. 18C, blue). From 10 to 20 seconds, the current decay was about 1% for both ferrocene oxidation and hydrazine oxidation, and 5% for proton reduction. The small difference at a long polarization time indicates that the current decay is mainly due to progressive surface contamination. The progressive surface contamination could also lead to current decrease in a successive potential pulses. In the case of hydrazine oxidation, we found that the current decay is more severe at Pt UMEs than at Au UMEs. The surface contamination at MNPs may be worse than at macroelectrodes because of their high relative surface area. This would be especially important for the hydrogen evolution reaction that depends upon adsorption of hydrogen atoms on Pt. Another mode that could cause current decay is the absorption of hydrogen atoms into the lattice of the Pt MNPs.

A similar current decrease at the Pt UME when the concentration of phosphate was increased to 200 mM has been seen indicating that the current decay was not due to the low concentration of supporting electrolyte, which favors the stability of MNPs. However, the current decay slows down appreciably at the Au UMEs, which indicates that the current decay is mostly correlated to the catalytic properties of Pt surface.

Figure 19A:
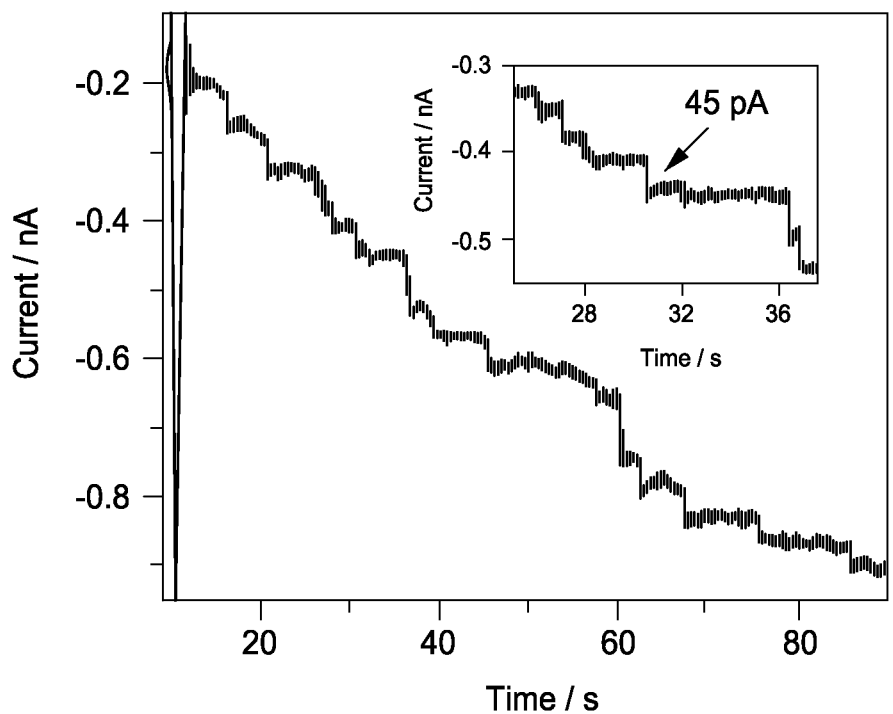
FIGS. 19A, 19B and 19C are graphs of the current transients recorded for individual Pt nanoparticle of different particle sizes.
Figure 19B:
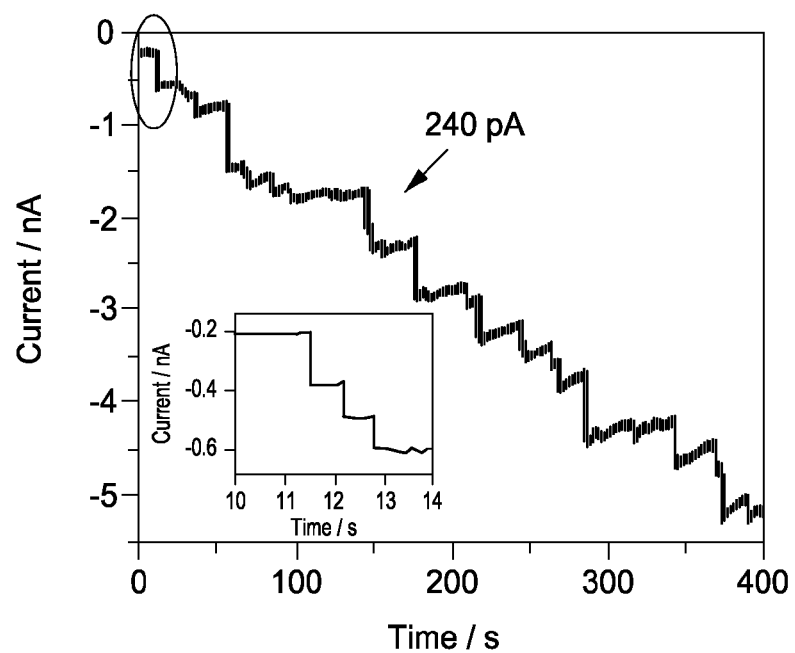
Figure 19C:
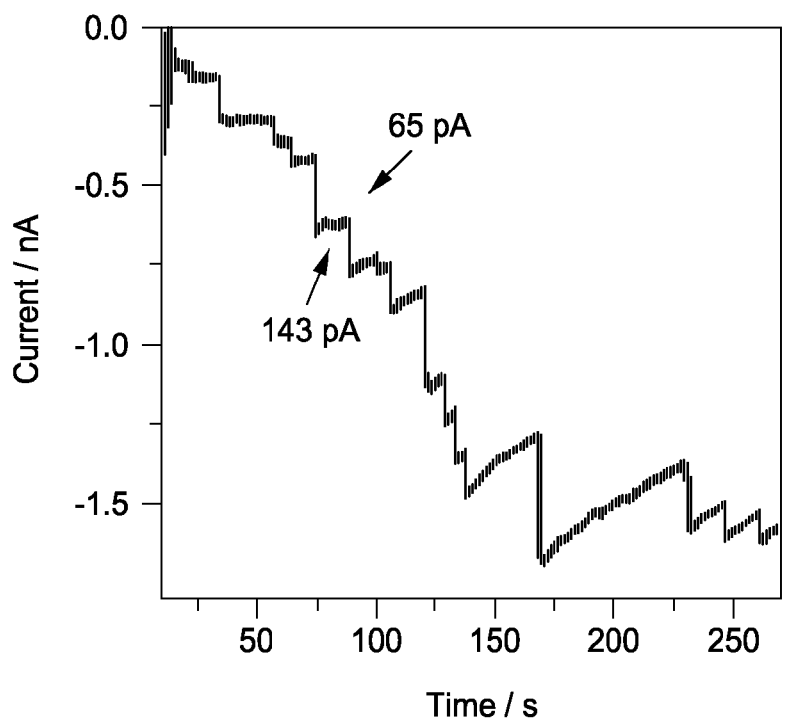
Figure 19D:
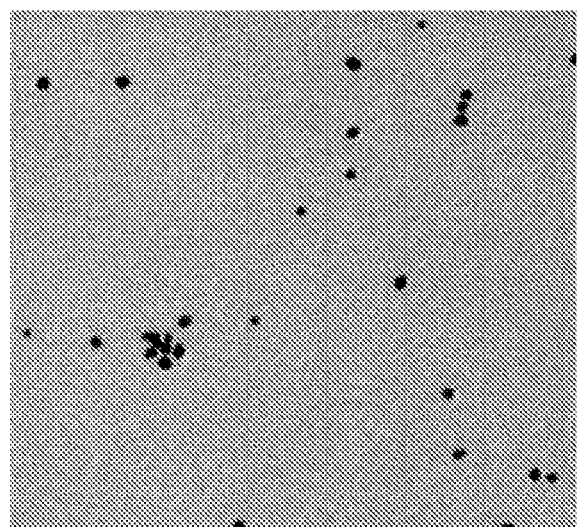
FIGS. 19D, 19E and 19F are TEM images which correspond to the individual Pt nanoparticle of the current transients graphs of FIGS. 19A, 19B and 19C respectively.
Figure 19E:
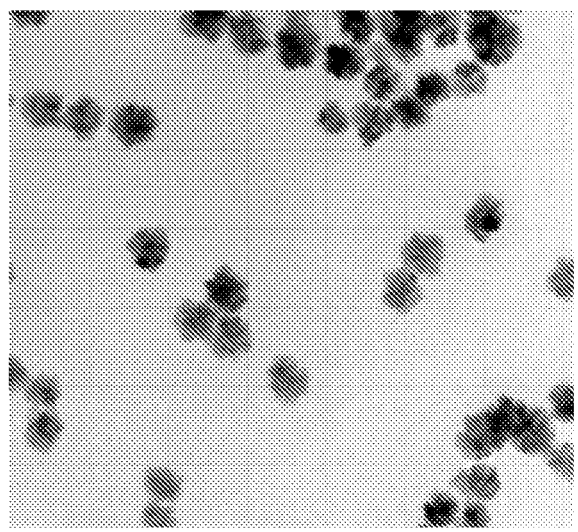
Figure 19F:
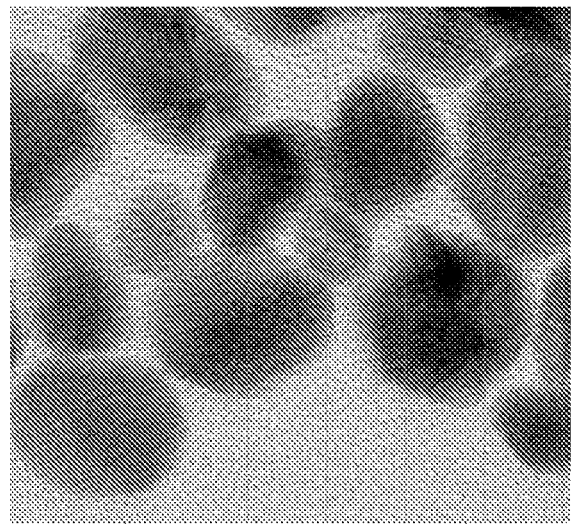

FIGS. 19A, 19B and 19C are graphs of the current transients recorded for individual Pt nanoparticle of different particle sizes. FIGS. 19D, 19E and 19F are TEM images which correspond to the individual Pt nanoparticle of the current transients graphs of FIGS. 19A, 19B and 19C respectively. The concentration based on Pt atom is about 50 nM in FIG. 19A, 500 nM in FIG. 19B, and 250 nM in FIG. 19C. With 10 µm Au UME in 12 mM hydrazine and 50 mM PBS buffer at a pH of about 7.5.

FIGS. 19A, 19B and 19C are graphs of the current transients recorded for individual Pt nanoparticle of different particle sizes. FIGS. 19D, 19E and 19F are TEM images which correspond to the individual Pt nanoparticle of the current transients graphs of FIGS. 19A, 19B and 19C respectively. FIG. 19 shows some representative current transients recorded for several Pt colloidal solutions with different particle sizes. Since the Pt NPs were stabilized by similar capping molecules, citrate or oxalate, they have similar catalytic properties. When injecting these NP solutions into the hydrazine test electrolyte, the recorded current transients show discrete current steps of very different current amplitudes. For about 3.6 nm, Pt NPs, the current steps had almost uniform amplitude which was mainly distributed around 45 pA (as seen in FIGS. 19A and 19D). In the case of star-like Pt NPs (as seen in FIGS. 19B and 19E), the peak currents were mainly distributed around 240 pA, corresponding to the particle size of about 20 nm. A small fraction of current peaks has peak current less than about 120 pA or larger than about 300 pA, probably due to the existence of small particles and aggregates of two to three units. FIG. 19C shows the current transient recorded for polydisperse Pt NPs as seen in FIG. 19F. The peak currents were distributed over a wide range between 60 and 200 pA, corresponding to particle sizes ranging from 5 to 16 nm. The amplitudes of the peak currents for the cases studied seem to correlate well with the particle size distribution.

Another possible application of MNP collisions is the evaluation of the porosity of insulating films. One can note the number of collisions compared with those at an uncovered electrode and the effect of MNP size using an Au UMEs with surface self-assembled monolayer films of alkane thiols. To differentiate particle collisions on the top of SAMs from those through pores within the SAMs, the Au detector electrode was modified with a C16SH monolayer which is long enough to inhibit the electron transfer through the monolayer. The porosity of the C16SH SAMs on Au was changed by varying the assembly time from 30 minutes to overnight. We also found that the degree of dryness of the Au substrate plays an important role in film quality, since the water layer remaining on the Au surface slows down the adsorption of hydrophobic molecules.

Figure 20A:
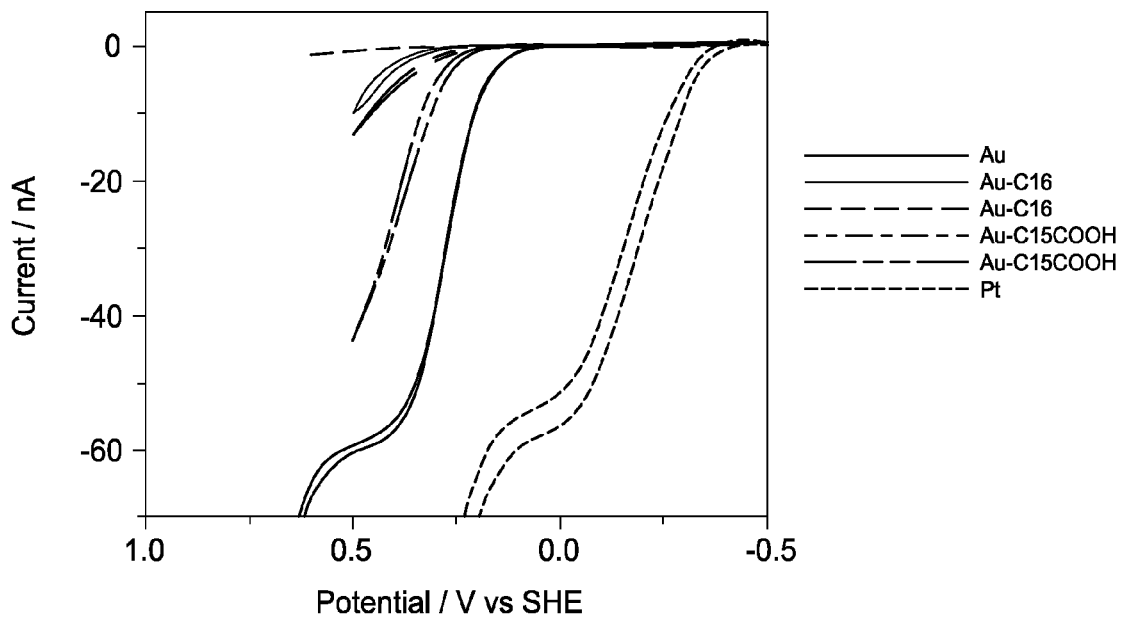
FIG. 20A is an image of a cyclic voltammogram and FIG. 20B is a graph of the current transients.
Figure 20B:
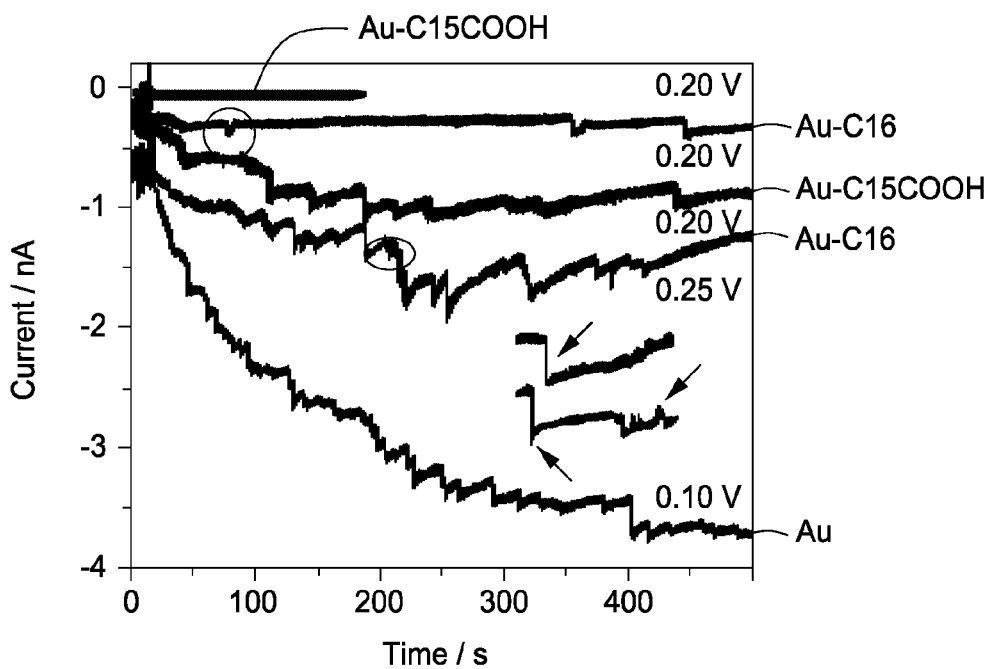

FIG. 20A is an image of a cyclic voltammogram and FIG. 20B is a graph of the current transients recorded at clean (black) and C16SH or HSC15COOH assembled Au UMEs, CV at Pt was plotted for comparison, with a scan rate of 100 mV/s. In addition, the traces in FIG. 20B were slightly offset for clarity. The inset figures show representative current profiles and very fast current fluctuations. The substrate potentials in chronoamperometry as indicated with 36 pM particle concentration and about 3.6 nm Pt particles and the solution contains 15 mM hydrazine in 50 mM PBS buffer, pH of about 7.5.

The quality of SAMs could be estimated directly from the suppression of hydrazine oxidation (as seen in FIG. 20A). Less porous films result in a greater suppression of hydrazine oxidation and thus smaller currents. FIG. 20A shows that not only the oxidation potential shifted positively, but also the oxidation current decreased as compared to a clean Au electrode at potentials negative of 0.5 V. From the extent of the suppression of hydrazine oxidation at these modified electrodes, the cyclic voltammograms indicate that HSC15COOH films are more porous than C16SH films.

However, since hydrazine is a small molecule, it is possibly able to penetrate all kinds of pores, thus the inhibition of hydrazine oxidation does not indicate the pore size distribution. The pore size distribution might be determined using size defined MNPs. As an example, we injected about 3.6 nm Pt NP solution into the same test electrolyte and recorded the current transients at these modified electrodes. The collision frequency or the number of collisions clearly decreased. Less porous films showed fewer collisions for both C16SH and HSC15COOH films. This is consistent with the suppression of hydrazine oxidation shown in cyclic voltammograms. No obvious collision or only very few collisions were observed when the surface was assembled with HSC15COOH and C16SH overnight.

At these modified electrodes, most of the current transients display a very long transient time, which might indicate that Pt NP is deactivated by the surrounding alkane thiols. Two typical transients are shown in the insert curves (shown in FIG. 20B and indicated by the black arrows). The alkane matrix might relocate from the Au to the Pt surfaces and thus prevent electrochemical hydrazine oxidation. Secondly, the current in many cases fluctuated back and forth rapidly with almost the same current amplitudes (shown in FIG. 20B and indicated by the red arrow), suggesting that the same particle may attach and detach from the Au surface. Such a fluctuation implies a weaker interaction of the particle with the electrode surface because of the surrounding matrix.

Comparison of C16SH with HSC15COOH films indicated fewer collisions but higher hydrazine oxidation peak currents were observed at the electrodes covered by HSC15COOH films. This indicates that microscopic pores in the film still allows for facile catalytic hydrazine oxidation but may not allow a MNP to pass through. In addition to the pore size, the exposed terminal carboxylic group may also play a role that prevents the MNPs penetration via the pores. More experiments with different particle sizes need to be carried out to confirm these effects and to understand which play important roles.

Electrocatalytic amplification allows the observation of single MNP collisions, characterized by individual current steps generated when the Pt NPs collide and stick at the detector electrode. The current result when the MNPs switch on an electrocatalytic reaction at their surfaces at a potential where the detector electrode shows negligibly small electrochemical activity. The observed current profiles during each collision are similar to those current transients recorded at UMEs and are a function of the NP radius. The kinetics of electrocatalytic reactions plays an important role in the observed current decay, which demands the exploration of more microscopic details related to the particle interaction with the electrode and the kinetics of electrocatalysis at the nanometer scale.

Because, at mass transport controlled conditions, the amplitude of each current step is correlated to the particle size, a plot of the current amplitudes versus the frequency of peak occurrence correlates well with the particle size distribution as found with TEM, thus providing an electrochemical approach to the rapid screening of NP dispersions. Since the collision frequency is also correlated to the effective surface area of the detector electrode, this technique may be useful in evaluating the porosity of insulating films on electrode surfaces.

The present invention contemplates the use of microelectrodes and ultramicroelectrodes and can be fabricated by methods known in the art, including semiconductor manufacturing methods and silk screening. The electrode may have a variety of size and shapes (e.g., disk, circular, square, rectangular, and oval) and as a result a variety of areas (e.g., an electrode can have an area of between about 5 $\mu m^2$ and about 3 $mm^2$). The electrode surface can be rough or smooth. In some embodiments, the electrode surface can be smooth to reduce the electrocatalytic rate for the redox reactant in the absence of nanoparticles.

A similar to or different counter/auxiliary/reference electrode can be used to complete the electrical circuit. In some embodiments, a 1 cm diameter graphite rode can be used as the counter electrode and the reference electrode can be saturated platinum-hydrogen or polypyrrole stainless-steel. Other common reference electrodes include Ag/AgCl. See Bard (2001) for details on these standard electrochemical techniques. The counter electrode, the optional reference electrode, and the electrode can be placed together in an electrochemical cell. The cell can also hold a solution that contains a redox reactant.

As used herein the term "redox reactant" as used herein, refers to a material in an electrochemical cell, distinct from the nanoparticle and the electrode that is capable of undergoing a reduction or oxidation reaction. In addition, nanoparticles that contact the electrode may become an electrocatalyst for a redox reactant in the solution. The redox reactant may be found in solution that contains charge carriers such as $Na^+$, $K^+$, $Ca^{2+}$, $Mg^{2+}$, $Cl^-$, $PO_3^{2-}$, $NH_4^+$. The solution can contain pH buffers. The solution can contain other compounds, such as surfactants, sugars, fats, proteins, etc. As used herein the term "electrocatalyst" as used herein refers to a material that is capable of amplifying the rate of electrochemical oxidation or reduction of a redox reactant. In at least one embodiment, contact between a nanoparticle and an electrode enables charge transfer between the nanoparticle and the electrode and enables the nanoparticle to become an electrocatalyst for the redox reactant. For a particular embodiment, the redox reactant can be selected in light of the nanoparticle and the electrode so that the nanoparticle acts as an electrocatalyst for the redox reactant, while the electrode has little to no electrocatalytic ability for the redox reactant. Exemplary redox reactants include methanol, hydrogen peroxide, and proton with platinum-containing nanoparticles and carbon-containing electrodes. Other exemplary redox reactants include hydrogen peroxide, proton, hydrazine, and oxygen with platinum-containing nanoparticles and gold-containing electrodes. Other exemplary redox reactants include tripropylamine with carbon-containing nanoparticles and a nickel-containing electrode.

A detector or array of detectors can be used to detect nanoparticle collisions with the electrode, via signal amplification from the electrocatalytic ability of the nanoparticle for the redox reactant, e.g., the detector can count the number of collisions, the detector can measure nanoparticle collisions by monitoring current changes or the detector can classify the collisions into one or more types (e.g., the magnitude of the current increase can be used to classify the nanoparticle). In various embodiments, the detector can measure nanoparticle collisions by monitoring potential changes. For example, the electrode can be driven with a constant current. In the absence of nanoparticles, the electrode voltage required to pass the current can be large. Upon a nanoparticle collision, the required voltage can drop substantially; thus, fast, large voltage drops can be interpreted as a nanoparticle collision. The magnitude of the voltage drop can be used classify the nanoparticle, for example, by nanoparticle size. The time response can also be used to classify the nanoparticle, for example, into different residence times.

The present invention includes methods, compositions and kits for analyzing a chemical analyte having an electrochemical cell connected to a measuring apparatus. The electrochemical cell contains a solution having one or more metal nanoparticles, one or more chemical analytes, an indicator. In addition, the electrochemical cell contains one or more electrodes in communication with the solution. One or more electrocatalytic properties are generated by the interaction of the one or more metal nanoparticles and the liquid sample and measured at the one or more electrodes.

The present invention includes one or more nanoparticles in solution within the electrochemical cell. The nanoparticles may be entirely or partially metal or a carbonaceous or semiconductor material. For example, the one or more metal nanoparticles may be platinum nanoparticles, gold nanoparticles, silver nanoparticles, copper nanoparticles, ruthenium nanoparticles, palladium nanoparticles or mixtures and combinations thereof. The nanoparticles may also have cores of a different material than the outer material of the nanoparticle. Although, the nanoparticles may be of in diameter sized between about 0.5 nm and about 100 nm, a common size range for one embodiment is between about 1 nm and 7 nm in diameter and an average of 4 nm in diameter. Furthermore, the size distribution of nanoparticle diameter may be generally uniform, disperse, or varying. The nanoparticles may have different groups of particles that have generally the same diameter within the group but differing diameter relative to other groups in solution.

The electrochemical reactions can be driven by controlling the electrical potential of the electrode. The electrical potential of the electrode can be selected so that oxidization or reduction can occur at the electrode. The potential can be set to minimize currents resulting from the redox reactant in the absence of nanoparticles and from other electrochemical reactions. The potential can be set with respect to a counter electrode or with respect to a reference electrode. See Bard (2001) for details on these standard electrochemical techniques. For example, the electrical potential can be within 1 V of zero, with respect to the standard hydrogen electrode (SHE). For example, the electrical potential can be within 1 V of zero, with respect to the counter electrode. Smaller voltage magnitudes (e.g., 0.5 V, 0.3 V, 0.25 V, or 0.1 V) may also be useful. The electrical potential may vary in time or be constant. In certain embodiments, a constant potential can be used to eliminate capacitive transients due to double-layer charging of the electrode. In some embodiments, a current can be driven through the electrode, and the potential can be monitored. Upon contact of a nanoparticle, the impedance and the voltage are greatly reduced. Other schemes for driving the electrochemical reactions needed to monitor the presence of nanoparticles will be evident to those skilled in the art.

Upon contact of the nanoparticle on the electrode, the reaction rate for the redox reactant greatly increases. For example, the rate of reaction of the redox reactant attributable to the nanoparticle normalized to the nanoparticle's surface area can be at least 200 times greater than the rate of reaction of the redox reactant attributable to the electrode normalized to the electrode's surface area. If measuring current, the above statement can be mathematically expressed as $(i_{NP}-i_e)/A_{NP} > 200 i_e/A_e$, where $i_{NP}$ is the current measured in the presence of a nanoparticle, $i_e$ is the current measured in the absence of a nanoparticle, and $A_{NP}$ and $A_e$ are the surface areas of the nanoparticle and electrode, respectively.

In some embodiments, the factor of increase is more than $10^3$, $10^4$, $10^5$, $10^6$, $10^7$, $10^8$, or $10^9$. The factor was about $10^6$, as calculated with a current attributable to nanoparticles of ~100 pA, a current attributable to the electrode of about 70 pA, and areas of 50 $\mu m^2$ and $5 \times 10^{-5}$ $\mu m^2$ for the electrode and nanoparticle respectively. The current generated at a constant potential can be large, because the redox reactant can be in high concentration and can be a fast diffuser. As an example, consider a disk electrode immersed in a dispersion of nanoparticles in a solution containing a redox reactant. The steady-state diffusion controlled flux of nanoparticles (NP) to the electrode surface, $J_{NP,e}$, is given by:

$$J_{NP,e} = 4D_{NP}C_{NP}/(pa) \quad (5)$$

where $D_{NP}$ is the nanoparticle diffusion coefficient, $C_{NP}$ is the nanoparticle concentration, and a is the radius of the electrode (Bard, 2001). Ordinarily, in a simple nanoparticle charging process, only one or a few electrons would transfer between the nanoparticles and the electrode ($n_{NP}$) to yield a current, $i_{NP,e} = n_{NP} F \pi a^2 J_{NP,e} = 4n_{NP} FaD_{NP}C_{NP}$, that is much too small to observe above the noise and background level (where F is the Faraday). However, the nanoparticles can electrocatalyze the redox reactant (RR) and, e.g., reduce or oxidize species RR to a product P, upon contact with the electrode so that a much larger current, $i_{RR}$, can flow. That is, when a nanoparticle collides with the electrode surface, it allows the reaction of RR to P at a potential where this reaction does not occur to any great degree at the electrode without a nanoparticle.

In some embodiments, a nanoparticle contacting the electrode can be detected. The steady-state diffusion-controlled current at the nanoparticle is given by:

$$i_{RR} = n_{RR} F_{ANP} J_{RR,NP} = B n_{RR} F D_{RR} C_{RR} r_{NP} \quad (6)$$

where $J_{RR,NP}$ is the flux of redox reactant RR to the nanoparticle, $D_{RR}$ is the diffusion coefficient of RR, $C_{RR}$ is the concentration of RR, $r_{NP}$ is the radius of the nanoparticle, and $n_{RR}$ is the number of electrons required per redox reaction for RR to be converted into product P. The factors $A_{NP}$, the nanoparticle surface area, and B, depend on the nanoparticle shape and how it is situated on the electrode. If it can be considered a sphere on an infinite plane, then $A_{NP} = 4\pi r_{NP}^2$ and $B = 4\pi \ln 2 \approx 8.71$ (Bobbert, 1987). Since $C_{RR}$ and $D_{RR}$ can be much larger than $C_{NP}$ and $D_{NP}$, even with the difference in a and $r_{NP}$, the current resulting from electrocatalysis of the redox reactant at a single nanoparticle can be ten orders of magnitude or more larger than the current resulting from capacitive charging the same nanoparticle at an electrode.

In various embodiments, the time response of electrode current can be measured. The current transient includes particle charging and a changing faradaic current for the electrocatalysis of redox reactant that attains steady state in a time $\sim r_{NP}^2/D_{RR}$. Since different types of collisions can occur, the current-time (i-t) transient for each collision event will be determined by the residence time of the nanoparticle at the electrode, i.e., the time period when the electrode can pass electrons to the nanoparticle. If the nanoparticle sticks to the electrode for a time sufficient for a steady state current to be attained, and the redox reactant is only converted to product at the particle, the amplification factor of the electrochemical current to charging current is given by the relative steady-state fluxes of the particles and RR is $\sim(B/16)(D_{RR}C_{RR}a)/(D_{NP}C_{NP}r_{NP})$. This will lead to relative steady-state currents of $\sim(BD_{RR}C_{RR}r_{NP})/(4D_{NP}C_{NP}a)$, assuming $n_{RR}=n_{NP}$. For a 1 pM nanoparticle and 10 mM redox reactant dispersion, the estimated amplification factor for a 1 nm radius particle can be nine to ten orders of magnitude, assuming the diffusion coefficient of the redox reactant is about an order of magnitude greater than that of the nanoparticle. Said another way, the current caused by the electrochemical conversion of the redox reactant to product can be nine to ten orders of magnitude larger than the capacitive charging current of the nanoparticles.

In addition, the present invention provides analysis of a sample using a concentrated solution of nanoparticles. The skilled artisan will recognize that depending on the particular parameter a wide range of nanoparticle concentrations (e.g., from the single nanoparticle to molar solutions) may be used by the present invention. In addition, mixtures of particles having different sizes, different particle compositions and different particles may be used with the present invention. The event is characterized by the current generated through the particle- The one or more electrocatalytic properties can be any property that can be measured by the apparatus; however, the most common property is an electrocatalytic amplification from a reduction or oxidation reaction catalyzed by the metal nanoparticles. Although, other property can be a current, a resistance, an impedance, a capacitance, an inductance or a combination thereof, or another technique that indicates an electron transfer reaction at an electrode.

Exemplary coating or capping compounds for stabilizing nanoparticles include alkanethiols, mercapto alcohols, mercaptocarboxylic acids, thiophenols, thiol-functionalized oligonucleotides, benzenedimethanethiol, oxalate, and citrate. Such stability-improving compounds are sufficiently small so that electron tunneling can still occur to enable charge transfer from the electrode to the nanoparticle.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Polsky, R; Gill, R; Kaganovsky, L; Willner, I, Analytical Chemistry, 2006, 78, 2268-2271.
2. Bard, A. J.; Faulkner, L. R. Electrochemical Methods, Fundamentals and Applications, 2nd ed.; John Wiley & Sons: New York, 2001.
3. Bobbert, P. A.; Wind, M. M.; Vlieger, J. Physica 1987 141A, 58-72.
4. Zhou, J. F.; Zu, Y. B.; Bard, A. J. J. Electroanal. Chem. 2000, 491, 22-29.
5. Yang, J.; Lee, J. Y.; Too, H. P. Anal. Chim. Acta 2006, 571, 206-210.
6. Xiao, X. Y.; Xu, B. Q.; Tao N. J. Nano Lett. 2004, 4, 267-271.
7. Sonnichsen, C.; Reinhard, B. M.; Liphardt, J.; et al. Nature Biotech. 2005, 23, 741-745.

What is claimed is:

1. A method of analyzing a sample comprising the steps of:
    adding one or more metal nanoparticles to a liquid sample to form a nanoparticle solution within a sample chamber comprising at least 2 electrodes individually have a diameter of between about 1 µm and about 2 mm;
    adding an indicator species capable of undergoing a heterogeneous electrocatalytic redox reaction in the nanoparticle solution;
    detecting a discrete electrocatalytic property from the electrochemical amplification which correlates to an individual discrete nanoparticle collision; and
    wherein the discrete electrocatalytic property is a discrete step or spike selected from at least one of electrical current, potential, charge, resistance, capacitance, inductance, impedance, light, and color.

2. The method of claim 1, wherein the reaction is an oxidation or reduction reaction comprising an electrocatalytic amplification at an individual one or more metal nanoparticles.

3. The method of claim 1, wherein the individual one or more metal individual nanoparticles comprises platinum nanoparticles, gold nanoparticles, silver nanoparticles, copper nanoparticles, ruthenium nanoparticles, palladium nanoparticles, tin oxide nanoparticles, carbon nanoparticles or a combination thereof.

4. The method of claim 1, wherein the at least 2 electrodes individually have an area of between about 1 µm$^2$ and about 1 mm$^2$.

5. The method of claim 1, wherein the nanoparticle comprises at least 50 atoms of an element selected from gold, platinum, palladium, rhodium, copper, silver, ruthenium, iron, aluminum, nickel, and tin.

6. The method of claim 1, further comprising at least one detector and additional detector an array of detectors, wherein the array of detectors can detect discrete transients independently.

7. The method of claim 1, wherein the electrochemical amplification is attributed by the distinguishable catalytic properties between nanoparticles and the detector electrodes wherein the rate of reaction at the individual one or more metal nanoparticles is at least 200 times greater than the rate of reaction at an electrode after normalizing.

8. The method of claim 1, wherein the nanoparticle solution has a concentration between 1 pM and 1 µM.

9. The method of claim 1, wherein the discrete transient is a step or a spike when recording by time.

10. The method of claim 1, wherein the discrete individual metal nanoparticle further comprises a coating.

11. The method of claim 1, wherein the discrete individual metal nanoparticle further comprise a coating of alkanethiols, mercapto alcohols, mercaptocarboxylic acids, thiophenols, thiol-functionalized oligonucleotides, benzenedimethanethiol, oxalate, or citrate.

12. The method of claim 1, further comprises oligonucleotides attached to the discrete individual metal nanoparticle.

13. The method of claim 1, wherein the nanoparticle solution has a concentration between 2 picomolar and 1 µM.

14. The method of claim 1, wherein the nanoparticle solution has a concentration between 3 picomolar and 1 µM.

15. A method of analyzing discrete individual nanoparticle reactions in a sample comprising the steps of:
    providing a sample chamber comprising at least 2 ultramicroelectrodes in a liquid sample;
    adding metal nanoparticles to a liquid sample to form a nanoparticle solution having less than a micromolar metal nanoparticle concentration;
    adding an indicator species to the nanoparticle solution, wherein the indicator species is capable of undergoing a heterogeneous electrocatalytic reaction;
    interacting a discrete individual nanoparticle with the indicator species and one of the at least 2 ultramicroelectrodes to generate a discrete transient, wherein the transient is a step or a spike of electrical current, an electrical potential, an electrical charge, an electrical resistance, an electrical capacitance, an electrical inductance, an electrical impedance, a light, and a color; and
    recording the discrete transient, wherein the discrete transient correlates to a discrete electrocatalytic reaction at a discrete individual nanoparticle.

16. A method of analyzing separate discrete individual nanoparticle reactions from 2 distinct reactions in a sample comprising the steps of:
    providing a sample chamber comprising at least 2 ultramicroelectrodes in a liquid sample;
    adding a first metal nanoparticle to a liquid sample to form a nanoparticle solution having less than a micromolar metal first nanoparticle concentration;
    adding a second metal nanoparticle to the nanoparticle solution having less than a micromolar second metal nanoparticle concentration;

adding a first indicator species to the nanoparticle solution, wherein the first indicator species is capable of undergoing a first electrocatalytic redox reaction with the first metal nanoparticle;

adding a second indicator species to the nanoparticle solution, wherein the second indicator species is capable of undergoing a second electrocatalytic redox reaction with the second metal nanoparticle;

interacting a discrete first individual nanoparticle with the first indicator species and one of the at least 2 ultramicroelectrodes to generate a first discrete electrocatalytic step current;

interacting a discrete second individual nanoparticle with the second indicator species and one of the at least 2 ultramicroelectrodes to generate a second discrete electrocatalytic step current;

observing the first discrete electrocatalytic step current that correlates to a first reaction of the discrete first individual nanoparticle; and observing the second discrete electrocatalytic step current that correlates to a second reaction of the discrete second individual nanoparticle.

\* \* \* \* \*